(12) United States Patent
Hans et al.

(10) Patent No.: US 7,220,418 B1
(45) Date of Patent: May 22, 2007

(54) DELIVERY OF TREFOIL PEPTIDES

(75) Inventors: Wolfgang Christian Hans, Landshut (DE); Lothar Steidler, Lokeren (BE); Erik René Remaut, Lonendegem (BE)

(73) Assignee: Vlaams Interuniversitair Instituut voor Biotechnologie (BE)

(*) Notice: Subject to any disclaimer, the term of this patent is extended or adjusted under 35 U.S.C. 154(b) by 150 days.

(21) Appl. No.: 10/030,390

(22) PCT Filed: Jul. 5, 2000

(86) PCT No.: PCT/EP00/06343

§ 371 (c)(1),
(2), (4) Date: Apr. 16, 2002

(87) PCT Pub. No.: WO01/02570

PCT Pub. Date: Jan. 11, 2001

(30) Foreign Application Priority Data

Jul. 5, 1999 (EP) .................... 99870143

(51) Int. Cl.
*A01N 63/00* (2006.01)
*A61K 39/02* (2006.01)
*A61K 39/00* (2006.01)

(52) U.S. Cl. .............. 424/200.1; 424/93.45; 424/93.2; 424/234.1; 424/192.1; 514/925

(58) Field of Classification Search ........... 424/200.1, 424/192.1, 184.1, 234.1, 244.1, 246.1, 93.2, 424/93.45; 514/2, 925; 435/69.3, 69.1, 435/71.1, 252.9
See application file for complete search history.

(56) References Cited

U.S. PATENT DOCUMENTS 6,221,648 B1 * 4/2001 Le Page et al. ......... 435/252.3
6,221,840 B1 * 4/2001 Podolsky .................. 514/12
6,605,286 B2 * 8/2003 Steidler et al. ......... 424/243.1

FOREIGN PATENT DOCUMENTS

| WO | WO 82/03329 | * 10/1982 |
| WO | WO 92/14837 | 9/1992 |
| WO | WO 93/17117 | * 2/1993 |
| WO | WO 97/09437 | 3/1997 |
| WO | WO 97/14806 | 4/1997 |
| WO | WO 97/38712 | 10/1997 |
| WO | WO 00/23471 | 4/2000 |
| WO | WO 01/21200 | * 3/2001 |

OTHER PUBLICATIONS

Malin et al. Ann. Nutr. Metabol. 40: 137-145, 1996.*
Wells et al. Mol. Microbiol. 8: 1155-1162, Jun. 1993.*
Wells et al. Appl. Environ. Microbiol. 59: 3954-3959, Nov. 1993.*
Babyatsky et al. Gastroenterology 110: 489-497, 1996.*
Playford et al. PNAS 93: 2137-2142, Mar. 1996.*
Chinery et al. Clin. Sci. 88: 401-403, 1995.*
Tran et al. Gut 44: 636-642, May 1999.*
Robinson et al. Nature Biotechnol. 15: 653-657, 1997.*
Pouwels et al. J. Biotechnol. 44: 183-192, 1992.*
Pouwels et al. Int. J. Food Microbiol. 41: 155-167, 1998.*
Steidler L. Nato ASI Series. vol. H98. Springer Verlag, Berlin Heidelberg, pp. 63-79, 1996.*
Wells et al. Antonie van Leeuwenhoek 70: 317-330, 1996.*
Slos et al. FEMS Microbiol. Lett. 169: 29-36, 1998.*
Steidler et al. Infect. Immun. 66: 3183-3189, 1998.*
Wong et al., *Int. J. Gastroenterology and Hepatology*, 44(6): 890-895, 1999.
Tan et al., *Biochem. and Biophys. Res. Communications*, 237: 673-677, 1997.
Lefebvre, *J. Cell. Biol.*, 122(1): 191-198, 1993.
Poulsen, S.S.; Thulesen, J.; Christensen, L.; NexØ, E.; and Thim, L., "Metabolism of Oral Trefoil Factor 2 (TFF2) and the Effect of Oral and Parenteral TFF2 on Gastric and Duodenal Ulcer Healing in the Rat", *Gut*, vol. 45, No. 2 (1999); pp. 516-522.

* cited by examiner

*Primary Examiner*—S. Devi
(74) *Attorney, Agent, or Firm*—Howrey LLP

(57) ABSTRACT

The present invention relates to a microorganism, preferably a bacterial strain, preferably a non-pathogenic strain, preferably a non-invasive strain, preferably a food grade strain, preferably a gram-positive bacterial strain, delivering a trefoil peptide in vivo. Preferably said trefoil peptide is TFF1. The present invention further relates to a method for the delivery of trefoil peptide to the gastro-intestinal tract comprising the administration of such a bacterial strain. The present invention also relates to a pharmaceutical composition comprising a trefoil peptide delivering bacterium as well as methods of treatment of acute gastro-intestinal inflammatory diseases comprising administration of said transformed bacterial strains, particularly for treating acute colitis, including but not limited to acute flare-ups of Crohn's disease and ulcerative colitis in humans, as well as for treating gastro-intestinal disorders of a similar nature in other animal species.

12 Claims, 16 Drawing Sheets

Figure 2A
pL2mTFF1v1 (SEQ ID NO 1)

```
GAATTCGAGCTCGGTACCCGGGGATCTCGATCCCGCGAAATTAATACGACTC
ACTATAGGGAGACCACAACGGTTTCCCTCTAGAAATAATTTTGTTTAACTTT
AAGAAGGAGATATACATATGAAAAAAAGATTATCTCAGCTATTTTAATGTC
TACAGTCATACTTTCTGCTGCAGCCCCGTTGTCAGGTGTTTACGCCCAGGCC
CAGGCCCAGGCCCAGGAAGAAACATGTATCATGGCCCCCCGGGAGAGGATAA
ATTGTGGCTTCCCCGGTGTCACCGCCCAGCAGTGCACGGAGAGAGGTTGCTG
TTTTGATGACAGTGTCCGGGGATTCCCGTGGTGCTTCCACCCCATGGCCATC
GAGAACACTCAAGAAGAAGAATGTCCCTTCTAACTAGTAGATCCGGCTGCTA
ACAAAGCCCGAAAGGAAGCTGAGTTGGCTGCTGCCACCGCTGAGCAATAACT
AGCATAACCCCTTGGGGCCTCTAAACGGGTCTTGAGGGGTTTTTTGCTGAAA
GGAGGAACTATATCCGGATGACCTGCAGGCATGCAAGCTTGGCACTGGCCGT
CGTTTTACAACGTCGTGACTGGGAAAACCCTGGCGTTACCCAACTTAATCGC
CTTGCAGCACATCCCCCTTTCGCCAGCTGATTTCACTTTTTGCATTCTACAA
ACTGCATAACTCATATGTAAATCGCTCCTTTTTAGGTGGCACAAATGTGAGG
CATTTTCGCTCTTTCCGGCGAGGCTAGTTACCCTTAAGTTATTGGTATGACT
GGTTTTAAGCGCAAAAAAAGTTGCTTTTTCGTACCTATTAATGTATCGTTTT
AGAAAACCGACTGTAAAAAGTACAGTCGGCATTATCTCATATTATAAAAGCC
AGTCATTAGGCCTATCTGACAATTCCTGAATAGAGTTCATAAACAATCCTGC
ATGATAACCATCACAAACAGAATGATGTACCTGTAAAGATAGCGGTAAATAT
ATTGAATTACCTTTATTAATGAATTTTCCTGCTGTAATAATGGGTAGAAGGT
AATTACTATTATTATTGATATTTAAGTTAAACCCAGTAAATGAAGTCCATGG
AATAATAGAAAGAGAAAAAGCATTTTCAGGTATAGGTGTTTTGGGAAACAAT
TTCCCCGAACCATTATATTTCTCTACATCAGAAAGGTATAAATCATAAAACT
CTTTGAAGTCATTCTTTACAGGAGTCCAAATACCAGAGAATGTTTTAGATAC
ACCATCAAAAATTGTATAAAGTGGCTCTAACTTATCCCAATAACCTAACTCT
CCGTCGCTATTGTAACCAGTTCTAAAAGCTGTATTTGAGTTTATCACCCTTG
TCACTAAGAAAATAAATGCAGGGTAAAATTTATATCCTTCTTGTTTTATGTT
TCGGTATAAAACACTAATATCAATTTCTGTGGTTATACTAAAAGTCGTTTGT
TGGTTCAAATAATGATTAAATATCTCTTTTCTCTTCCAATTGTCTAAATCAA
TTTTATTAAAGTTCATTTGATATGCCTCCTAAATTTTTATCTAAAGTGAATT
TAGGAGGCTTACTTGTCTGCTTTCTTCATTAGAATCAATCCTTTTTTAAAAG
TCAATATTACTGTAACATAAATATATATTTTAAAAATATCCCACTTTATCCA
ATTTTCGTTTGTTGAACTAATGGGTGCTTTAGTTGAAGAATAAAGACCACAT
TAAAAAATGTGGTCTTTTGTGTTTTTTTAAAGGATTTGAGCGTAGCGAAAAA
TCCTTTTCTTTCTTATCTTGATAATAAGGGTAACTATTGCCGGGATAGACTG
TAACATTCTCACGCATAAAATCCCCTTTCATTTTCTAATGTAAATCTATTAC
CTTATTATTAATTCAATTCGCTCATAATTAATCCTTTTTCTTATTACGCAAA
ATGGCCCGATTTAAGCACACCCTTTATTCCGTTAATGCGCCATGACAGCCAT
GATAATTACTAATACTAGGAGAAGTTAATAAATACGTAACCAACATGATTAA
CAATTATTAGAGGTCATCGTTCAAAATGGTATGCGTTTTGACACATCCACTA
TATATCCGTGTCGTTCTGTCCACTCCTGAATCCCATTCCAGAAATTCTCTAG
CGATTCCAGAAGTTTCTCAGAGTCGGAAAGTTGACCAGACATTACGAACTGG
CACAGATGGTCATAACCTGAAGGAAGATCTGATTGCTTAACTGCTTCAGTTA
AGACCGAAGCGCTCGTCGTATAACAGATGCGATGATGCAGACCAATCAACAT
GGCACCTGCCATTGCTACCTGTACAGTCAAGGATGGTAGAAATGTTGTCGGT
CCTTGCACACGAATATTACGCCATTTGCCTGCATATTCAAACAGCTCTTCTA
CGATAAGGGCACAAATCGCATCGTGGAACGTTTGGGCTTCTACCGATTTAGC
AGTTTGATACACTTTCTCTAAGTATCCACCTGAATCATAAATCGGCAAAATA
GAGAAAAATTGACCATGTGTAAGCGGCCAATCTGATTCCACCTGAGATGCAT
```

Figure 2B

```
AATCTAGTAGAATCTCTTCGCTATCAAAATTCACTTCCACCTTCCACTCACC
GGTTGTCCATTCATGGCTGAACTCTGCTTCCTCTGTTGACATGACACACATC
ATCTCAATATCCGAATAGGGCCCATCAGTCTGACGACCAAGAGAGCCATAAA
CACCAATAGCCTTAACATCATCCCCATATTTATCCAATATTCGTTCCTTAAT
TTCATGAACAATCTTCATTCTTTCTTCTCTAGTCATTATTATTGGTCCATTC
ACTATTCTCATTCCCTTTTCAGATAATTTTAGATTTGCTTTTCTAAATAAGA
ATATTTGGAGAGCACCGTTCTTATTCAGCTATTAATAACTCGTCTTCCTAAG
CATCCTTCAATCCTTTTAATAACAATTATAGCATCTAATCTTCAACAAACTG
GCCCGTTTGTTGAACTACTCTTTAATAAAATAATTTTTCCGTTCCCAATTCC
ACATTGCAATAATAGAAAATCCATCTTCATCGGCTTTTTCGTCATCATCTGT
ATGAATCAAATCGCCTTCTTCTGTGTCATCAAGGTTTAATTTTTTATGTATT
TCTTTTAACAAACCACCATAGGAGATTAACCTTTTACGGTGTAAACCTTCCT
CCAAATCAGACAAACGTTTCAAATTCTTTTCTTCATCATCGGTCATAAAATC
CGTATCCTTTACAGGATATTTTGCAGTTTCGTCAATTGCCGATTGTATATCC
GATTTATATTTATTTTTCGGTATTTTTTATTAAAACGTCTCAAAATCGTTTC
TGGGACGTTTTAGCGTTTATTTCGTTTAGTTATCGGCATAATCGTTAAAACA
GGCGTTATCGTAGCGTAAAAGCCCTTGAGCGTAGCGTGCTTTGCAGCGAAGA
TGTTGTCTGTTAGATTATGAAAGCCGATGACTGAATGAAATAATAAGCGCAG
CGTCCTTCTATTTCGGTTGGAGGAGGCTCAAGGGAGTTTGAGGGAATGAAAT
TCCCTCATGGGTTTGATTTTAAAAATTGCTTGCAATTTTGCCGAGCGGTAGC
GCTGGAAAATTTTTGAAAAAAATTTGGAATTTGGAAAAAAATGGGGGGAAAG
GAAGCGAATTTTGCTTCCGTACTACGACCCCCCATTAAGTGCCGAGTGCCAA
TTTTTGTGCCAAAAACGCTCTATCCCAACTGGCTCAAGGGTTTGAGGGGTTT
TTCAATCGCCAACGAATCGCCAACGTTTTCGCCAACGTTTTTTATAAATCTA
TATTTAAGTAGCTTTATTGTTGTTTTTATGATTACAAAGTGATACACTAATT
TTATAAAATTATTTGATTGGAGTTTTTTAAATGGTGATTTCAGAAATCGAAAA
AAAGAGTTATGATTTCTCTGACAAAAGAGCAAGATAAAAAATTAACAGATAT
GGCGAAACAAAAAGGTTTTTTCAAAATCTGCGGTTGCGGCGTTAGCTATAGAA
GAATATGCAAGAAAGGAATCAGAACAAAAAAAATAAGCGAAAGCTCGCGTTT
TTAGAAGGATACGAGTTTTCGCTACTTGTTTTTGATAAGGTAATATATCATG
GCTATTAAAAATACTAAAGCTAGAAATTTTGGATTTTTATTATATCCTGACT
CAATTCCTAATGATTGGAAAGAAAAATTAGAGAGTTTGGGCGTATCTATGGC
TGTCAGTCCTTTACACGATATGGACGAAAAAAAAGATAAAGATACATGGAAT
AGTAGTGATGTTATACGAAATGGAAAGCACTATAAAAAACCACACTATCACG
TTATATATATTGCACGAAATCCTGTAACAATAGAAAGCGTTAGGAACAAGAT
TAAGCGAAAATTGGGGAATAGTTCAGTTGCTCATGTTGAGATACTTGATTAT
ATCAAAGGTTCATATGAATATTTGACTCATGAATCAAAGGACGCTATTGCTA
AGAATAAACATATATACGACAAAAAGATATTTTGAACATTAATGATTTTGA
TATTGACCGCTATATAACACTTGATGAAAGCCAAAAAAGAGAATTGAAGAAT
TTACTTTTAGATATAGTGGATGACTATAATTTGGTAAATACAAAAGATTTAA
TGGCTTTTATTCGCCTTAGGGGAGCGGAGTTTGGAATTTTAAATACGAATGA
TGTAAAAGATATTGTTTCAACAAACTCTAGCGCCTTTAGATTATGGTTTGAG
GGCAATTATCAGTGTGGATATAGAGCAAGTTATGCAAAGGTTCTTGATGCTG
AAACGGGGGAAATAAAATGACAAACAAAGAAAAGAGTTATTTGCTGAAAAT
GAGGAATTAAAAAAAGAAATTAAGGACTTAAAAGAGCGTATTGAAAGATACA
GAGAAATGGAAGTTGAATTAAGTACAACAATAGATTTATTGAGAGGAGGGAT
TATTGAATAAATAAAAGCCCCCCTGACGAAAGTCGCGACTTCGTTCTTTTTT
TACCTCTCGGTTATGAGTTAGTTCAAATTCGTTCTTTTTAGGTTCTAAATCG
TGTTTTTCTTGGAATTGTGCTGTTTTATCCTTTACCTTGTCTACAAACCCCT
TAAAAACGTTTTTAAAGGCTTTTAAGCCGTCTGTACGTTCCTTAAG
```

Figure 3A
pT1mTFF1 (SEQ ID NO 2)

```
GAATTCGATTAAGTCATCTTACCTCTTTTATTAGTTTTTTCTTATAATCTAA
TGATAACATTTTTATAATTAATCTATAAACCATATCCCTCTTTGGAATCAAA
ATTTATTATCTACTCCTTTGTAGATATGTTATAATACAAGTATCAGATCTGG
GAGACCACAACGGTTTCCCACTAGAAATAATTTTGTTTAACTTTAGAAAGGA
GATATACGCATGAAAAAAAAGATTATCTCAGCTATTTTAATGTCTACAGTCA
TACTTTCTGCTGCAGCCCCGTTGTCAGGTGTTTACGCCCAGGCCCAGGCCCA
GGCCCAGGCCCAGGAAGAAACATGTATCATGGCCCCCGGGAGAGGATAAAT
TGTGGCTTCCCCGGTGTCACCGCCCAGCAGTGCACGGAGAGAGGTTGCTGTT
TTGATGACAGTGTCCGGGGATTCCCGTGGTGCTTCCACCCCATGGCCATCGA
GAACACTCAAGAAGAAGAATGTCCCTTCTAACTAGTAGATCCGGCTGCTAAC
AAAGCCCGAAAGGAAGCTGAGTTGGCTGCTGCCACCGCTGAGCAATAACTAG
CATAACCCCTTGGGGCCTCTAAACGGGTCTTGAGGGGTTTTTTGCTGAAAGG
AGGAACTATATCCGGATGACCTGCAGGCAAGCTCTAGAATCGATACGATTTT
GAAGTGGCAACAGATAAAAAAAAGCAGTTTAAAATTGTTGCTGAACTTTTAA
AACAAGCAAATACAATCATTGTCGCAACAGATAGCGACAGAGAAGGCGAAAA
CATTGCCTGGTCGATCATTCATAAAGCAAATGCCTTTTCTAAAGATAAAACG
TATAAAAGACTATGGATCAATAGTTTAGAAAAAGATGTGATCCGTAGCGGTT
TTCAAAATTTGCAACCAGGAATGAATTACTATCCCTTTTATCAAGAAGCGCA
AAAGAAAAACGAAATGATACACCAATCAGTGCAAAAAAAGATATAATGGGAG
ATAAGACGGTTCGTGTTCGTGCTGACTTGCACCATATCATAAAAATCGAAAC
AGCAAAGAATGGCGGAAACGTAAAAGAAGTTATGGAAATAAGACTTAGAAGC
AAACTTAAGAGTGTGTTGATAGTGCAGTATCTTAAAATTTTGTATAATAGGA
ATTGAAGTTAAATTAGATGCTAAAAATTTGTAATTAAGAAGGAGTGATTACA
TGAACAAAAATATAAAATATTCTCAAAACTTTTTAACGAGTGAAAAAGTACT
CAACCAAATAATAAAACAATTGAATTTAAAAGAAACCGATACCGTTTACGAA
ATTGGAACAGGTAAAGGGCATTTAACGACGAAACTGGCTAAAATAAGTAAAC
AGGTAACGTCTATTGAATTAGACAGTCATCTATTCAACTTATCGTCAGAAAA
ATTAAAACTGAATACTCGTGTCACTTTAATTCACCAAGATATTCTACAGTTT
CAATTCCCTAACAAACAGAGGTATAAAATTGTTGGGAGTATTCCTTACCATT
TAAGCACACAAATTATTAAAAAAGTGGTTTTTGAAAGCCATGCGTCTGACAT
CTATCTGATTGTTGAAGAAGGATTCTACAAGCGTACCTTGGATATTCACCGA
ACACTAGGGTTGCTCTTGCACACTCAAGTCTCGATTCAGCAATTGCTTAAGC
TGCCAGCGGAATGCTTTCATCCTAAACCAAAAGTAAACAGTGTCTTAATAAA
ACTTACCCGCCATACCACAGATGTTCCAGATAAATATTGGAAGCTATATACG
TACTTTGTTTCAAAATGGGTCAATCGAGAATATCGTCAACTGTTTACTAAAA
ATCAGTTTCATCAAGCAATGAAACACGCCAAAGTAAACAATTTAAGTACCGT
TACTTATGAGCAAGTATTGTCTATTTTTAATAGTTATCTATTATTTAACGGG
AGGAAATAATTCTATGAGTCGCTTTTGTAAATTTGGAAAGTTACACGTTACT
AAAGGGAATGTAGATAAATTATTAGGTATACTACTGACAGCTTCCAAGGAGC
TAAAGAGGTCCCTAGCGCTCTTATCATGGGGAAGCTCGGATCATATGCAAGA
CAAAATAAACTCGCAACAGCACTTGGAGAAATGGGACGAATCGAGAAAACCC
TCTTTACGCTGGATTACATATCTAATAAAGCCGTAAGGAGACGGGTTCAAAA
AGGTTTAAATAAAGGAGAAGCAATCAATGCATTAGCTAGAACTATATTTTTT
GGACAACGTGGAGAATTTAGAGAACGTGCTCTCCAAGACCAGTTACAAAGAG
CTAGTGCACTAAACATAATTATTAACGCTATAAGTGTGTGGAACACTGTATA
TATGGAAAAAGCCGTAGAAGAATTAAAAGCAAGAGGAGAATTTAGAGAAGAT
TTAATGCCATATGCGTGGCCGTTAGGATGGGAACATATCAATTTTCTTGGAG
AATACAAATTTGAAGGATTACATGACACTGGGCAAATGAATTTACGTCCTTT
ACGTATAAAAGAGCCGTTTTATTCTTAATATAACGGCTCTTTTTATAGAAAA
```

Figure 3B

```
AATCCTTAGCGTGGTTTTTTTCCGAAATGCTGGCGGTACCCCAAGAATTAGA
AATGAGTAGATCAAATTATTCACGAATAGAATCAGGAAAATCAGATCCAACC
ATAAAAACACTAGAACAAATTGCAAAGTTAACTAACTCAACGCTAGTAGTGG
ATTTAATCCCAAATGAGCCAACAGAACCAGAGCCAGAAACAGAATCAGAACA
AGTAACATTGGATTTAGAAATGGAAGAAGAAAAAAGCAATGACTTCGTGTGA
ATAATGCACGAAATCGTTGCTTATTTTTTTTTAAAAGCGGTATACTAGATAT
AACGAAACAACGAACTGAATAGAAACGAAAAAAGAGCCATGACACATTTATA
AAATGTTTGACGACATTTTATAAATGCATAGCCCGATAAGATTGCCAAACCA
ACGCTTATCAGTTAGTCAGATGAACTCTTCCCTCGTAAGAAGTTATTTAATT
AACTTTGTTTGAAGACGGTATATAACCGTACTATCATTATATAGGGAAATCA
GAGAGTTTTCAAGTATCTAAGCTACTGAATTTAAGAATTGTTAAGCAATCAA
TCGGAAATCGTTTGATTGCTTTTTTTTGTATTCATTTATAGAAGGTGGAGTTT
GTATGAATCATGATGAATGTAAAACTTATATAAAAAATAGTTTATTGGAGAT
AAGAAAATTAGCAAATATCTATACACTAGAAACGTTTAAGAAAGAGTTAGAA
AAGAGAAATATCTACTTAGAAACAAAATCAGATAAGTATTTTTCTTCGGAGG
GGGAAGATTATATATAAGTTAATAGAAAATAACAAAATAATTTATTCGAT
TAGTGGAAAAAAATTGACTTATAAAGGAAAAAAATCTTTTTCAAAACATGCA
ATATTGAAACAGTTGAATGAAAAAGCAAACCAAGTTAATTAAACAACCTATT
TTATAGGATTTATAGGAAAGGAGAACAGCTGAATGAATATCCCTTTTGTTGT
AGAAACTGTGCTTCATGACGGCTTGTTAAAGTACAAATTTAAAAATAGTAAA
ATTCGCTCAATCACTACCAAGCCAGGTAAAAGCAAAGGGGCTATTTTTGCGT
ATCGCTCAAAATCAAGCATGATTGGCGGTCGTGGTGTTGTTCTGACTTCCGA
GGAAGCGATTCAAGAAAATCAAGATACATTTACACATTGGACACCCAACGTT
TATCGTTATGGAACGTATGCAGACGAAAACCGTTCATACACGAAAGGACATT
CTGAAAACAATTTAAGACAAATCAATACCTTCTTTATTGATTTTGATATTCA
CACGGCAAAAGAAACTATTTCAGCAAGCGATATTTTAACAACCGCTATTGAT
TTAGGTTTTATGCCTACTATGATTATCAAATCTGATAAAGGTTATCAAGCAT
ATTTTGTTTTAGAAACGCCAGTCTATGTGACTTCAAAATCAGAATTTAAATC
TGTCAAAGCAGCCAAAATAATTTCGCAAAATATCCGAGAATATTTTGGAAAG
TCTTTGCCAGTTGATCTAACGTGTAATCATTTTGGTATTGCTCGCATACCAA
GAACGGACAATGTAGAATTTTTTGATCCTAATTACCGTTATTCTTTCAAAGA
ATGGCAAGATTGGTCTTTCAAACAAACAGATAATAAGGGCTTTACTCGTTCA
AGTCTAACGGTTTTAAGCGGTACAGAAGGCAAAAAACAAGTAGATGAACCCT
GGTTTAATCTCTTATTGCACGAAACGAAATTTTCAGGAGAAAAGGGTTTAAT
AGGGCGTAATAACGTCATGTTTACCCTCTCTTTAGCCTACTTTAGTTCAGGC
TATTCAATCGAAACGTGCGAATATAATATGTTTGAGTTTAATAATCGATTAG
ATCAACCCTTAGAAGAAAAGAAGTAATCAAAATTGTTAGAAGTGCCTATTC
AGAAAACTATCAAGGGGCTAATAGGGAATACATTACCATTCTTTGCAAAGCT
TGGGTATCAAGTGATTTAACCAGTAAAGATTTATTTGTCCGTCAAGGGTGGT
TTAAATTCAAGAAAAAAAGAAGCGAACGTCAACGTGTTCATTTGTCAGAATG
GAAAGAAGATTTAATGGCTTATATTAGCGAAAAAAGCGATGTATACAAGCCT
TATTTAGTGACGACCAAAAAAGAGATTAGAGAAGTGCTAGGCATTCCTGAAC
GGACATTAGATAAATTGCTGAAGGTACTGAAGGCGAATCAGGAAATTTTCTT
TAAGATTAAACCAGGAAGAAATGGTGGCATTCAACTTGCTAGTGTTAAATCA
TTGTTGCTATCGATCATTAAAGTAAAAAAAGAAGAAAAAGAAAGCTATATAA
AGGCGCTGACAAATTCTTTTGACTTAGAGCATACATTCATTCAAGAGACTTT
AAACAAGCTAGCAGAACGCCCTAAAACGGACACACAACTCGATTTGTTTAGC
TATGATACAGGCTGAAAATAAAACCCGCACTATGCCATTACATTTATATCTA
TGATACGTGTTTGTTTTTTCTTTGCTGTTTAGCGAATGATTAGCAGAAATAT
ACAGAGTAAGATTTTAATTAATTATTAGGGGGAGAAGGAGAGAGTAGCCCGA
```

Figure 3C

AAACTTTTAGTTGGCTTGGACTGAACGAAGTGAGGGAAAGGCTACTAAAACG
TCGAGGGGCAGTGAGAGCGAAGCGAACACTTGATTTTTTAATTTTCTATCTT
TTATAGGTCATTAGAGTATACTTATTTGTCCTATAAACTATTTAGCAGCATA
ATAGATTTATTGAATAGGTCATTTAAGTTGAGCATATTAGAGGAGGAAAATC
TTGGAGAAATATTTGAAGAACCCGATTACATGGATTGGATTAGTTCTTGTGG
TTACGTGGTTTTTAACTAAAAGTAGTGAATTTTTGATTTTTGGTGTGTGTGT
CTTGTTGTTAGTATTTGCTAGTCAAAGTGATTAAATA

Figure 4A
pPICmTFF1 (SEQ ID NO 3)

AGATCTAACATCCAAAGACGAAAGGTTGAATGAAACCTTTTTGCCATCCGACATCCAC
AGGTCCATTCTCACACATAAGTGCCAAACGCAACAGGAGGGGATACACTAGCAGCA
GACCGTTGCAAACGCAGGACCTCCACTCCTCTTCTCCTCAACACCCACTTTTGCCAT
CGAAAAACCAGCCCAGTTATTGGGCTTGATTGGAGCTCGCTCATTCCAATTCCTTCTA
TTAGGCTACTAACACCATGACTTTATTAGCCTGTCTATCCTGGCCCCCCTGGCGAGG
TTCATGTTTGTTTATTTCCGAATGCAACAAGCTCCGCATTACACCCGAACATCACTCC
AGATGAGGGCTTTCTGAGTGTGGGGTCAAATAGTTTCATGTTCCCCAAATGGCCCAA
AACTGACAGTTTAAACGCTGTCTTGGAACCTAATATGACAAAAGCGTGATCTCATCCA
AGATGAACTAAGTTTGGTTCGTTGAAATGCTAACGGCCAGTTGGTCAAAAAGAAACTT
CCAAAAGTCGCCATACCGTTTGTCTTGTTTGGTATTGATTGACGAATGCTCAAAAATA
ATCTCATTAATGCTTAGCGCAGTCTCTCTATCGCTTCTGAACCCCGGTGCACCTGTG
CCGAAACGCAAATGGGGAAACACCCGCTTTTTGGATGATTATGCATTGTCTCCACATT
GTATGCTTCCAAGATTCTGGTGGGAATACTGCTGATAGCCTAACGTTCATGATCAAAA
TTTAACTGTTCTAACCCCTACTTGACAGCAATATATAAACAGAAGGAAGCTGCCCTGT
CTTAAACCTTTTTTTTTATCATCATTATTAGCTTACTTTCATAATTGCGACTGGTTCCAA
TTGACAAGCTTTTGATTTTAACGACTTTTAACGACAACTTGAGAAGATCAAAAAACAAC
TAATTATTCGAAGGATCCAAACGATGAGATTTCCTTCAATTTTTACTGCAGTTTTATTC
GCAGCATCCTCCGCATTAGCTGCTCCAGTCAACACTACAACAGAAGATGAAACGGCA
CAAATTCCGGCTGAAGCTGTCATCGGTTACTCAGATTTAGAAGGGGATTTCGATGTT
GCTGTTTTGCCATTTTCCAACAGCACAAATAACGGGTTATTGTTTATAAATACTACTAT
TGCCAGCATTGCTGCTAAAGAAGAAGGGGTATCTCTCGAGAAAAGAGAGGCTGAAG
CCCAGGCCCAGGCCCAGGCCCAGGCCCAGGAAGAAACATGTATCATGGCCCCCG
GGAGAGGATAAATTGTGGCTTCCCCGGTGTCACCGCCCAGCAGTGCACGGAGAGAG
GTTGCTGTTTTGATGACAGTGTCCGGGGATTCCCGTGGTGCTTCCACCCCATGGCCA
TCGAGAACACTCAAGAAGAAGAATGTCCCTTCTAACTAGTGGCGTAGAATTCCCTAG
GGCGGCCGCGAATTAATTCGCCTTAGACATGACTGTTCCTCAGTTCAAGTTGGGCAC
TTACGAGAGACCGGTCTTGCTAGATTCTAATCAAGAGGATGTCAGAATGCCATTTG
CCTGAGAGATGCAGGCTTCATTTTTGATACTTTTTTATTTGTAACCTATATAGTATAGG
ATTTTTTTTGTCATTTTGTTTCTTCTCGTACGAGCTTGCTCCTGATCAGCCTATCTCGC
AGCTGATGAATATCTTGTGGTAGGGGTTTGGGAAAATCATTCGAGTTTGATGTTTTTC
TTGGTATTTCCCACTCCTCTTCAGAGTACAGAAGATTAAGTGAGAAGTTCGTTTGTGC
AAGCTTATCGATAAGCTTTAATGCGGGTAGTTTATCACAGTTAAATTGCTAACGCAGTC
AGGCACCGTGTATGAAATCTAACAATGCGCTCATCGTCATCCTCGGCACCGTCACCC
TGGATGCTGTAGGCATAGGCTTGGTTATGCCGGTACTGCCGGGCCTCTTGCGGGAT
ATCGTCCATTCCGACAGCATCGCCAGTCACTATGGCGTGCTGCTAGCGCTATATGCG
TTGATGCAATTTCTATGCGCACCCGTTCTCGGAGCACTGTCCGACCGCTTTGGCCGC
CGCCCAGTCCTGCTCGCTTCGCTACTTGGAGCCACTATCGACTACGCGATCATGGC
GACCACACCCGTCCTGTGGATCTATCGAATCTAAATGTAAGTTAAAATCTCTAAATAA
TTAAATAAGTCCCAGTTTCTCCATACGAACCTTAACAGCATTGCGGTGAGCATCTAGA
CCTTCAACAGCAGCCAGATCCATCACTGCTTGGCCAATATGTTTCAGTCCCTCAGGA
GTTACGTCTTGTGAAGTGATGAACTTCTGGAAGGTTGCAGTGTTAACTCCGCTGTATT
GACGGGCATATCCGTACGTTGGCAAAGTGTGGTTGGTACCGGAGGAGTAATCTCCA
CAACTCTCTGGAGAGTAGGCACCAACAAACACAGATCCAGCGTGTTGTACTTGATCA
ACATAAGAAGAAGCATTCTCGATTTGCAGGATCAAGTGTTCAGGAGCGTACTGATTG
GACATTTCCAAAGCCTGCTCGTAGGTTGCAACCGATAGGGTTGTAGAGTGTGCAATA
CACTTGCGTACAATTTCAACCCTTGGCAACTGCACAGCTTGGTTGTAACAGCATCTT
CAATTCTGGCAAGCTCCTTGTCTGTCATATCGACAGCCAACAGAATCACCTGGGAAT
CAATACCATGTTCAGCTTGAGACAGAAGGTCTGAGGCAACGAAATCTGGATCAGCGT

Figure 4B

```
ATTTATCAGCAATAACTAGAACTTCAGAAGGCCCAGCAGGCATGTCAATACTACACAG
GGCTGATGTGTCATTTTGAACCATCATCTTGGCAGCAGTAACGAACTGGTTTCCTGG
ACCAAATATTTTGTCACACTTAGGAACAGTTTCTGTTCCGTAAGCCATAGCAGCTACT
GCCTGGGCGCCTCCTGCTAGCACGATACACTTAGCACCAACCTTGTGGGCAACGTA
GATGACTTCTGGGGTAAGGGTACCATCCTTCTTAGGTGGAGATGCAAAAACAATTTC
TTTGCAACCAGCAACTTTGGCAGGAACACCCAGCATCAGGGAAGTG
GAAGGCAGAATTGCGGTTCCACCAGGAATATAGAGGCCAACTTTCTCAATAGGTCTT
GCAAAACGAGAGCAGACTACACCAGGGCAAGTCTCAACTTGCAACGTCTCCGTTAGT
TGAGCTTCATGGAATTTCCTGACGTTATCTATAGAGATCAATGGCTCTCTTAACGT
TATCTGGCAATTGCATAAGTTCCTCTGGGAAAGGAGCTTCTAACACAGGTGTCTTCAA
AGCGACTCCATCAAACTTGGCAGTTAGTTCTAAAAGGGCTTTGTCACCATTTTGACGA
ACATTGTCGACAATTGGTTTGACTAATTCCATAATCTGTTCCGTTTTCTGGATAGGAC
GACGAAGGGCATCTTCAATTTCTTGTGAGGAGGCCTTAGAAACGTCAATTTTGCACA
ATTCAATACGACCTTCAGAAGGGACTTCTTTAGGTTTGGATTCTTCTTTAGGTTGTTC
CTTGGTGTATCCTGGCTTGGCATCTCCTTTCCTTCTAGTGACCTTTAGGGACTTCATA
TCCAGGTTTCTCTCCACCTCGTCCAACGTCACACCGTACTTGGCACATCTAACTAATG
CAAAATAAAATAAGTCAGCACATTCCCAGGCTATATCTTCCTTGGATTTAGCTTCTGC
AAGTTCATCAGCTTCCTCCCTAATTTTAGCGTTCAACAAAACTTCGTCGTCAAATAAC
CGTTTGGTATAAGAACCTTCTGGAGCATTGCTCTTACGATCCCACAAGGTGGCTTCC
ATGGCTCTAAGACCCTTTGATTGGCCAAAACAGGAAGTGCGTTCCAAGTGACAGAAA
CCAACACCTGTTTGTTCAACCACAAATTTCAAGCAGTCTCCATCACAATCCAATTCGA
TACCCAGCAACTTTTGAGTTGCTCCAGATGTAGCACCTTTATACCACAAACCGTGACG
ACGAGATTGGTAGACTCCAGTTTGTGTCCTTATAGCCTCCGGAATAGACTTTTTGGAC
GAGTACACCAGGCCCAACGAGTAATTAGAAGAGTCAGCCACCAAAGTAGTGAATAGA
CCATCGGGGCGGTCAGTAGTCAAAGACGCCAACAAAATTTCACTGACAGGGAACTTT
TTGACATCTTCAGAAAGTTCGTATTCAGTAGTCAATTGCCGAGCATCAATAATGGGGA
TTATACCAGAAGCAACAGTGGAAGTCACATCTACCAACTTTGCGGTCTCAGAAAAAG
CATAAACAGTTCTACTACCGCCATTAGTGAAACTTTTCAAATCGCCCAGTGGAGAAGA
AAAAGGCACAGCGATACTAGCATTAGCGGGCAAGGATGCAACTTTATCAACCAGGGT
CCTATAGATAACCCTAGCGCCTGGGATCATCCTTTGGACAACTCTTTCTGCCAAATCT
AGGTCCAAAATCACTTCATTGATACCATTATTGTACAACTTGAGCAAGTTGTCGATCA
GCTCCTCAAATTGGTCCTCTGTAACGGATGACTCAACTTGCACATTAACTTGAAGCTC
AGTCGATTGAGTGAACTTGATCAGGTTGTGCAGCTGGTCAGCAGCATAGGGAAACAC
GGCTTTTCCTACCAAACTCAAGGAATTATCAAACTCTGCAACACTTGCGTATGCAGGT
AGCAAGGGAAATGTCATACTTGAAGTCGGACAGTGAGTGTAGTCTTGAGAAATTCTG
AAGCCGTATTTTTATTATCAGTGAGTCAGTCATCAGGAGATCCTCTACGCCGGACGC
ATCGTGGCCCGACCTGCAGGTCGGCATCACCGGCGCCACAGGTGCGGTTGCTGGCG
CCTATATCGCCGACATCACCGATGGGGAAGATCGGGCTCGCCACTTCGGGCTCATG
AGCGCTTGTTTCGGCGTGGGTATGGTGGCAGGCCCCGTGGCCGGGGACTGTTGG
GCGCCATCTCCTTGCATGCACCATTCCTTGCGGCGGCGGTGCTCAACGGCCTCAAC
CTACTACTGGGCTGCTTCCTAATGCAGGAGTCGCATAAGGGAGAGCGTCGAGTATCT
ATGATTGGAAGTATGGGAATGGTGATACCCGCATTCTTCAGTGTCTTGAGGTCTCCT
ATCAGATTATGCCCAACTAAAGCAACCGGAGGAGGAGATTTCATGGTAAATTTCTCTG
ACTTTTGGTCATCAGTAGACTCGAACTGTGAGACTATCTCGGTTATGACAGCAGAAAT
GTCCTTCTTGGAGACAGTAAATGAAGTCCCACCAATAAAGAAATCCTTGTTATCAGGA
ACAAACTTCTTGTTTCGAACTTTTTCGGTGCCTTGAACTATAAAATGTAGAGTGGATAT
GTCGGGTAGGAATGGAGCGGGCAAATGCTTACCTTCTGGACCTTCAAGAGGTATGTA
GGGTTTGTAGATACTGATGCCAACTTCAGTGACAACGTTGCTATTTCGTTCAAACCAT
TCCGAATCCAGAGAAATCAAAGTTGTTTGTCTACTATTGATCCAAGCCAGTGCGGTCT
TGAAACTGACAATAGTGTGCTCGTGTTTTGAGGTCATCTTTGTATGAATAAATCTAGT
```

Figure 4C

```
CTTTGATCTAAATAATCTTGACGAGCCAAGGCGATAAATACCCAAATCTAAAACTCTTT
TAAAACGTTAAAAGGACAAGTATGTCTGCCTGTATTAAACCCCAAATCAGCTCGTAGT
CTGATCCTCATCAACTTGAGGGGCACTATCTTGTTTTAGAGAAATTTGCGGAGATGC
GATATCGAGAAAAAGGTACGCTGATTTTAAACGTGAAATTTATCTCAAGATCTCTGCC
TCGCGCGTTTCGGTGATGACGGTGAAAACCTCTGACACATGCAGCTCCCGGAGACG
GTCACAGCTTGTCTGTAAGCGGATGCCGGGAGCAGACAAGCCCGTCAGGGCGCGT
CAGCGGGTGTTGGCGGGTGTCGGGGCGCAGCCATGACCCAGTCACGTAGCGATAG
CGGAGTGTATACTGGCTTAACTATGCGGCATCAGAGCAGATTGTACTGAGAGTGCAC
CATATGCGGTGTGAAATACCGCACAGATGCGTAAGGAGAAAATACCGCATCAGGCG
CTCTTCCGCTTCCTCGCTCACTGACTCGCTGCGCTCGGTCGTTCGGCTGCGGCGAG
CGGTATCAGCTCACTCAAAGGCGGTAATACGGTTATCCACAGA
ATCAGGGGATAACGCAGGAAAGAACATGTGAGCAAAAGGCCAGCAAAAGGCCAGGA
ACCGTAAAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAA
CTACGGCTACACTAGAAGGACAGTATTTGGTATCTGCGCTCTGCTGAAGCCAGTTAC
CTTCGGAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAG
GGATTTTGGTCATGAGATTATCAAAAAGGATCTTCACCTAGATCCTTTTAAATTAAAAA
TGAAGTTTTAAATCAATCTAAAGTATATATGAGTAAACTTGGTCTGACAGTTACCAATG
CTTAATCAGTGAGGCACCTATCTCAGCGATCTGTCTATTTCGTTCATCCATAGTTGCC
TGACTCCCCGTCGTGTAGATAACTACGATACGGGAGGGCTTACCATCTGGCCCCAGT
GCTGCAATGATACCGCGAGACCCACGCTCACCGGCTCCAGATTTATCAGCAATAAAC
CAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTG
CGCAACGTTGTTGCCATTGCTGCAGGCATCGTGGTGTCACGCTCGTCGTTTGGTATG
GCTTCATTCAGCTCCGGTTCCCAACGATCAAGGCGAGTTACATGATCCCCCATGTTG
TGCAAAAAAGCGGTTAGCTCCTTCGGTCCTCCGATCGTTGTCAGAAGTAAGTTGGCC
GCAGTGTTATCACTCATGGTTATGGCAGCACTGCATAATTCTCTTACTGTCATGCCAT
CCGTAAGATGCTTTTCTGTGACTGGTGAGTACTCAACCAAGTCATTCTGAGAATAGTG
TATGCGGCGACCGAGTTGCTCTTGCCCGGCGTCAACACGGGATAATACCGCGCCAC
ATAGCAGAACTTTAAAAGTGCTCATCATTGGAAAACGTTCTTCGGGGCGAAAACTCTC
AAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTCTTC
CTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAGTG
CCACCTGACGTCTAAGAAACCATTATTATCATGACATTAACCTATAAAAATAGGCGTA
TCACGAGGCCCTTTCGTCTTCAAGAATTAATTCTCATGTTTGACAGCTTATCATCGAT
AAGCTGACTCATGTTGGTATTGTGAAATAGACGCAGATCGGGAACACTGAAAAATAA
CAGTTATTATTCG
```

Distal Colon

SEQUENCE LISTING

```
<160> NUMBER OF SEQ ID NOS: 5

<210> SEQ ID NO 1
<211> LENGTH: 5142
<212> TYPE: DNA
<213> ORGANISM: Artificial Sequence
<220> FEATURE:
<223> OTHER INFORMATION: Synthetic

<400> SEQUENCE: 1
```

-continued

```
gaattcgagc tcggtacccg gggatctcga tcccgcgaaa ttaatacgac tcactatagg        60
gagaccacaa cggtttccct ctagaaataa ttttgtttaa ctttaagaag gagatataca       120
tatgaaaaaa aagattatct cagctatttt aatgtctaca gtcatacttt ctgctgcagc       180
cccgttgtca ggtgtttacg cccaggccca ggcccaggcc caggaagaaa catgtatcat       240
ggccccccgg gagaggataa attgtggctt cccoggtgtc accgcccagc agtgcacgga       300
gagaggttgc tgttttgatg acagtgtccg gggattcccg tggtgcttcc accccatggc       360
catcgagaac actcaagaag aagaatgtcc cttctaacta gtagatccgg ctgctaacaa       420
agcccgaaag gaagctgagt tggctgctgc caccgctgag caataactag cataacccct       480
tggggcctct aaacgggtct tgagggggttt tttgctgaaa ggaggaacta tatccggatg      540
acctgcaggc atgcaagctt ggcactggcc gtcgttttac aacgtcgtga ctgggaaaac       600
cctggcgtta cccaacttaa tcgccttgca gcacatcccc ctttcgccag ctgatttcac       660
tttttgcatt ctacaaactg cataactcat atgtaaatcg ctccttttta ggtggcacaa       720
atgtgaggca ttttcgctct ttccggcgag gctagttacc cttaagttat tggtatgact       780
ggttttaagc gcaaaaaaag ttgcttttc gtacctatta atgtatcgtt ttagaaaacc        840
gactgtaaaa agtacagtcg gcattatctc atattataaa agccagtcat taggcctatc       900
tgacaattcc tgaatagagt tcataaacaa tcctgcatga taaccatcac aaacagaatg      960
atgtacctgt aaagatagcg gtaaatatat tgaattacct ttattaatga attttcctgc      1020
tgtaataatg ggtagaaggt aattactatt attattgata tttaagttaa acccagtaaa      1080
tgaagtccat ggaataatag aaagagaaaa agcattttca ggtataggtg ttttgggaaa      1140
caatttcccc gaaccattat atttctctac atcagaaagg tataaatcat aaaactcttt      1200
gaagtcattc tttacaggag tccaaatacc agagaatgtt ttagatacac catcaaaaat      1260
tgtataaagt ggctctaact tatcccaata acctaactct ccgtcgctat tgtaaccagt      1320
tctaaaagct gtatttgagt ttatcaccct tgtcactaag aaaataaatg cagggtaaaa      1380
tttatatcct tcttgtttta tgtttcggta taaaacacta atatcaattt ctgtggttat      1440
actaaaagtc gtttgttggt tcaaataatg attaaatatc tcttttctct tccaattgtc      1500
taaatcaatt ttattaaagt tcatttgata tgcctcctaa atttttatct aaagtgaatt      1560
taggaggctt acttgtctgc tttcttcatt agaatcaatc cttttttaaa agtcaatatt      1620
actgtaacat aaatatatat tttaaaaata tcccacttta tccaattttc gtttgttgaa      1680
ctaatgggtg ctttagttga agaataaaga ccacattaaa aaatgtggtc ttttgtgttt      1740
ttttaaggga tttgagcgta gcgaaaaatc cttttctttc ttatcttgat aataagggta      1800
actattgccg ggatagactg taacattctc acgcataaaa tccccttttca ttttctaatg     1860 taaatctatt accttattat taattcaatt cgctcataat taatccttttt tcttattacg     1920 caaaatggcc cgatttaagc acacccttta ttccgttaat gcgccatgac agccatgata      1980
attactaata ctaggagaag ttaataaata cgtaaccaac atgattaaca attattagag      2040
gtcatcgttc aaaatggtat gcgttttgac acatccacta tatatccgtg tcgttctgtc      2100
cactcctgaa tcccattcca gaattctct agcgattcca gaagtttctc agagtcggaa       2160
agttgaccag acattacgaa ctggcacaga tggtcataac ctgaaggaag atctgattgc      2220
ttaactgctt cagttaagac cgaagcgctc gtcgtataac agatgcgatg atgcagacca      2280
atcaacatgg cacctgccat tgctacctgt acagtcaagg atggtagaaa tgttgtcggt      2340
```

-continued

```
ccttgcacac gaatattacg ccatttgcct gcatattcaa acagctcttc tacgataagg    2400
gcacaaatcg catcgtggaa cgtttgggct tctaccgatt tagcagtttg atacactttc    2460
tctaagtatc cacctgaatc ataaatcggc aaaatagaga aaaattgacc atgtgtaagc    2520
ggccaatctg attccacctg agatgcataa tctagtagaa tctcttcgct atcaaaattc    2580
acttccacct tccactcacc ggttgtccat tcatggctga actctgcttc ctctgttgac    2640
atgacacaca tcatctcaat atccgaatag ggcccatcag tctgacgacc aagagagcca    2700
taaacaccaa tagccttaac atcatcccca tatttatcca atattcgttc cttaatttca    2760
tgaacaatct tcattctttc ttctctagtc attattattg gtccattcac tattctcatt    2820 ccctttcag ataattttag atttgctttt ctaaataaga atatttggag agcaccgttc      2880
ttattcagct attaataact cgtcttccta agcatccttc aatcctttta ataacaatta    2940
tagcatctaa tcttcaacaa actggcccgt tgttgaact actctttaat aaaataattt      3000
ttccgttccc aattccacat tgcaataata gaaaatccat cttcatcggc ttttcgtca      3060 tcatctgtat gaatcaaatc gccttcttct gtgtcatcaa ggtttaattt tttatgtatt    3120
tcttttaaca aaccaccata ggagattaac cttttacggt gtaaaccttc ctccaaatca    3180
gacaaacgtt tcaaattctt ttcttcatca tcggtcataa aatccgtatc ctttacagga    3240
tattttgcag tttcgtcaat tgccgattgt atatccgatt tatatttatt tttcggtatt    3300
ttttattaaa acgtctcaaa atcgtttctg ggacgtttta gcgtttattt cgtttagtta    3360
tcggcataat cgttaaaaca ggcgttatcg tagcgtaaaa gcccttgagc gtagcgtgct    3420
ttgcagcgaa gatgttgtct gttagattat gaaagccgat gactgaatga aataataagc    3480
gcagcgtcct tctatttcgg ttggaggagg ctcaagggag tttgagggaa tgaaattccc    3540
tcatgggttt gattttaaaa attgcttgca attttgccga gcggtagcgc tggaaaattt    3600
ttgaaaaaaa tttggaattt ggaaaaaaat gggggaaag gaagcgaatt ttgcttccgt      3660
actacgaccc cccattaagt gccgagtgcc aattttgtg ccaaaacgc tctatcccaa       3720 ctggctcaag ggtttgaggg gttttttcaat cgccaacgaa tcgccaacgt tttcgccaac    3780
gttttttata aatctatatt taagtagctt tattgttgtt tttatgatta caaagtgata    3840
cactaatttt ataaaattat ttgattggag ttttttaaat ggtgatttca gaatcgaaaa    3900
aaagagttat gatttctctg acaaaagagc aagataaaaa attaacagat atggcgaaac    3960
aaaaaggttt ttcaaaatct gcggttgcgg cgttagctat agaagaatat gcaagaaagg    4020
aatcagaaca aaaaaaataa gcgaaagctc gcgttttttag aaggatacga gttttcgcta    4080 cttgttttg ataaggtaat atatcatggc tattaaaaat actaaagcta gaaattttgg       4140
atttttatta tatcctgact caattcctaa tgattggaaa gaaaaattag agagtttggg    4200
cgtatctatg gctgtcagtc ctttacacga tatggacgaa aaaaagata aagatacatg     4260 gaatagtagt gatgttatac gaaatggaaa gcactataaa aaaccacact atcacgttat    4320
atatattgca cgaaatcctg taacaataga aagcgttagg aacaagatta agcgaaaatt    4380
ggggaatagt tcagttgctc atgttgagat acttgattat atcaaaggtt catatgaata    4440
tttgactcat gaatcaaagg acgctattgc taagaataaa catatatacg acaaaaaaga    4500
tattttgaac attaatgatt ttgatattga ccgctatata acacttgatg aaagccaaaa    4560
aagagaattg aagaatttac ttttagatat agtggatgac tataatttgg taaatacaaa    4620
agatttaatg gcttttattc gccttagggg agcggagttt ggaattttaa atacgaatga    4680
tgtaaaagat attgtttcaa caaactctag cgcctttaga ttatggtttg agggcaatta    4740
```

```
tcagtgtgga tatagagcaa gttatgcaaa ggttcttgat gctgaaacgg gggaaataaa      4800
atgacaaaca agaaaaaga gttatttgct gaaaatgagg aattaaaaaa agaaattaag      4860
gacttaaaag agcgtattga agatacagaa gaaatggaag ttgaattaag tacaacaata    4920
gatttattga gaggagggat tattgaataa ataaaagccc ccctgacgaa agtcgcgact    4980
tcgttctttt tttacctctc ggttatgagt tagttcaaat tcgttctttt taggttctaa    5040
atcgtgtttt tcttggaatt gtgctgtttt atcctttacc ttgtctacaa accccttaaa    5100
aacgttttta aaggctttta agccgtctgt acgttcctta ag                      5142
```

<210> SEQ ID NO 2
<211> LENGTH: 5497
<212> TYPE: DNA
<213> ORGANISM: Artificial Sequence
<220> FEATURE:
<223> OTHER INFORMATION: Synthetic

<400> SEQUENCE: 2

```
gaattcgatt aagtcatctt acctctttta ttagtttttt cttataatct aatgataaca      60 ttttataat taatctataa accatatccc tctttggaat caaaatttat tatctactcc      120
tttgtagata tgttataata caagtatcag atctgggaga ccacaacggt ttcccactag    180
aaataatttt gtttaacttt agaaaggaga tatacgcatg aaaaaaaaga ttatctcagc    240
tattttaatg tctacagtca tactttctgc tgcagccccg ttgtcaggtg tttacgccca    300
ggcccaggcc caggcccagg cccaggaaga aacatgtatc atggcccccc gggagaggat    360
aaattgtggc ttccccggtg tcaccgccca gcagtgcacg gagagaggtt gctgttttga    420
tgacagtgtc cggggattcc cgtggtgctt ccaccccatg gccatcgaga acactcaaga    480
agaagaatgt cccttctaac tagtagatcc ggctgctaac aaagcccgaa aggaagctga    540
gttggctgct gccaccgctg agcaataact agcataaccc cttggggcct ctaaacgggt    600
cttgaggggt tttttgctga aggaggaac tatatccgga tgacctgcag gcaagctcta    660
gaatcgatac gattttgaag tggcaacaga taaaaaaaag cagtttaaaa ttgttgctga    720
acttttaaaa caagcaaata caatcattgt cgcaacagat agcgacagag aaggcgaaaa    780
cattgcctgg tcgatcattc ataaagcaaa tgccttttct aaagataaaa cgtataaaag    840
actatggatc aatagtttag aaaaagatgt gatccgtagc ggttttcaaa atttgcaacc    900
aggaatgaat tactatccct tttatcaaga agcgcaaaag aaaaacgaaa tgatacacca    960
atcagtgcaa aaaagatat aatgggagat aagacggttc gtgttcgtgc tgacttgcac    1020
catatcataa aaatcgaaac agcaaagaat ggcggaaacg taaagaagt tatgaaaata    1080 agacttagaa gcaaacttaa gagtgtgttg atagtgcagt atcttaaaat tttgtataat    1140
aggaattgaa gttaaattag atgctaaaaa tttgtaatta agaaggagtg attacatgaa    1200
caaaaatata aatattctc aaaactttt aacgagtgaa aaagtactca accaaataat    1260 aaacaattg aatttaaaag aaaccgatac cgtttacgaa attggaacag gtaaagggca    1320
tttaacgacg aaactggcta aaataagtaa acaggtaacg tctattgaat tagacagtca    1380
tctattcaac ttatcgtcag aaaaattaaa actgaatact cgtgtcactt taattccacca    1440 agatattcta cagtttcaat tccctaacaa acagaggtat aaaattgttg ggagtattcc    1500
ttaccattta agcacacaaa ttattaaaaa agtggttttt gaaagccatg cgtctgacat    1560
ctatctgatt gttgaagaag gattctacaa gcgtaccttg atattcacc gaacactagg    1620
```

-continued

```
gttgctcttg cacactcaag tctcgattca gcaattgctt aagctgccag cggaatgctt      1680
tcatcctaaa ccaaaagtaa acagtgtctt aataaaactt acccgccata ccacagatgt      1740
tccagataaa tattggaagc tatatacgta ctttgtttca aaatgggtca atcgagaata      1800
tcgtcaactg tttactaaaa atcagtttca tcaagcaatg aaacacgcca aagtaaacaa      1860
tttaagtacc gttacttatg agcaagtatt gtctattttt aatagttatc tattatttaa      1920
cgggaggaaa taattctatg agtcgctttt gtaaatttgg aaagttacac gttactaaag      1980
ggaatgtaga taaattatta ggtatactac tgacagcttc caaggagcta aagaggtccc      2040
tagcgctctt atcatgggga agctcggatc atatgcaaga caaataaaac tcgcaacagc      2100
acttggagaa atgggacgaa tcgagaaaac cctctttacg ctggattaca tatctaataa      2160
agccgtaagg agacgggttc aaaaaggttt aaataaagga gaagcaatca atgcattagc      2220
tagaactata ttttttggac aacgtggaga atttagagaa cgtgctctcc aagaccagtt      2280
acaaagagct agtgcactaa acataattat taacgctata agtgtgtgga acactgtata      2340
tatggaaaaa gccgtagaag aattaaaagc aagaggagaa tttagagaag atttaatgcc      2400
atatgcgtgg ccgttaggat gggaacatat caatttcctt ggagaataca aatttgaagg      2460
attacatgac actgggcaaa tgaatttacg tcctttacgt ataaaagagc cgttttattc      2520
ttaatataac ggctcttttt atagaaaaaa tccttagcgt ggtttttttc cgaaatgctg      2580
gcggtacccc aagaattaga aatgagtaga tcaaattatt cacgaataga atcaggaaaa      2640
tcagatccaa ccataaaaac actagaacaa attgcaaagt taactaactc aacgctagta      2700
gtggatttaa tcccaaatga gccaacagaa ccagagccag aaacagaatc agaacaagta      2760
acattggatt tagaaatgga agaagaaaaa agcaatgact tcgtgtgaat aatgcacgaa      2820
atcgttgctt atttttttt aaaagcggta tactagatat aacgaaacaa cgaactgaat      2880
agaaacgaaa aaagagccat gacacattta taaaatgttt gacgcacttt tataaatgca      2940
tagcccgata agattgccaa accaacgctt atcagttagt cagatgaact cttccctcgt      3000
aagaagttat ttaattaact ttgtttgaag acggtatata accgtactat cattatatag      3060
ggaaatcaga gagttttcaa gtatctaagc tactgaattt aagaattgtt aagcaatcaa      3120
tcggaaatcg tttgattgct ttttttgtat tcatttatag aaggtggagt ttgtatgaat      3180
catgatgaat gtaaaactta tataaaaaat agtttattgg agataagaaa attagcaaat      3240
atctatacac tagaaacgtt taagaaagag ttagaaaaga gaaatatcta cttagaaaca      3300
aaatcagata agtattttc ttcggagggg gaagattata tatataagtt aatagaaaat      3360
aacaaaataa tttattcgat tagtggaaaa aaattgactt ataaaggaaa aaaatctttt      3420
tcaaaacatg caatattgaa acagttgaat gaaaaagcaa accaagttaa ttaaacaacc      3480
tattttatag gatttatagg aaaggagaac agctgaatga atatcccttt tgttgtagaa      3540
actgtgcttc atgacggctt gttaaagtac aaatttaaaa atagtaaaat tcgctcaatc      3600
actaccaagc caggtaaaag caaaggggct atttttgcgt atcgctcaaa atcaagcatg      3660
attggcggtc gtggtgttgt tctgacttcc gaggaagcga ttcaagaaaa tcaagataca      3720
tttacacatt ggacacccaa cgtttatcgt tatggaacgt atgcagacga aaaccgttca      3780
tacacgaaag gacattctga aaacaattta agacaaatca ataccttctt tattgattt       3840 gatattcaca cggcaaaaga aactatttca gcaagcgata ttttaacaac cgctattgat      3900 ttaggttta tgcctactat gattatcaaa tctgataaag gttatcaagc atattttgtt       3960
ttagaaacgc cagtctatgt gacttcaaaa tcagaattta aatctgtcaa agcagccaaa      4020
```

-continued

| | | | | |
|---|---|---|---|---|
|ataatttcgc|aaaatatccg|agaatatttt|ggaaagtctt|tgccagttga tctaacgtgt|4080|
|aatcattttg|gtattgctcg|cataccaaga|acggacaatg|tagaattttt tgatcctaat|4140|
|taccgttatt|ctttcaaaga|atggcaagat|tggtctttca|aacaaacaga taataagggc|4200|
|tttactcgtt|caagtctaac|ggttttaagc|ggtacagaag|gcaaaaaaca agtagatgaa|4260|
|ccctggttta|atctcttatt|gcacgaaacg|aaattttcag|gagaaagggg tttaataggg|4320|
|cgtaataacg|tcatgtttac|cctctcttta|gcctacttta|gttcaggcta ttcaatcgaa|4380|
|acgtgcgaat|ataatatgtt|tgagtttaat|aatcgattag|atcaacccct agaagaaaaa|4440|
|gaagtaatca|aaattgttag|aagtgcctat|tcagaaaact|atcaagggge taatagggaa|4500|
|tacattacca|ttctttgcaa|agcttgggta|tcaagtgatt|taaccagtaa agatttattt|4560|
|gtccgtcaag|ggtggtttaa|attcaagaaa|aaaagaagcg|aacgtcaacg tgttcatttg|4620|
|tcagaatgga|agaagatttt|aatggcttat|attagcgaaa|aaagcgatgt atacaagcct|4680|
|tatttagtga|cgaccaaaaa|agagattaga|gaagtgctag|gcattcctga acggacatta|4740|
|gataaattgc|tgaaggtact|gaaggcgaat|caggaaattt|tctttaagat taaaccagga|4800|
|agaaatggtg|gcattcaact|tgctagtgtt|aaatcattgt|tgctatcgat cattaaagta|4860|
|aaaaaagaag|aaaaagaaag|ctatataaag|gcgctgacaa|attcttttga cttagagcat|4920|
|acattcattc|aagagacttt|aaacaagcta|gcagaacgcc|ctaaaacgga cacacaactc|4980|
|gatttgttta|gctatgatac|aggctgaaaa|taaaacccgc|actatgccat acatttata|5040|
|tctatgatac|gtgtttgttt|tttctttgct|gtttagcgaa|tgattagcag aaatatacag|5100|
|agtaagattt|taattaatta|ttaggggag|aaggagagag|tagcccgaaa acttttagtt|5160|
|ggcttggact|gaacgaagtg|agggaaaggc|tactaaaacg|tcgaggggca gtgagagcga|5220|
|agcgaacact|tgatttttta|attttctatc|ttttataggt|cattagagta tacttatttg|5280|
|tcctataaac|tatttagcag|cataatagat|ttattgaata|ggtcatttaa gttgagcata|5340|
|ttagaggagg|aaaatcttgg|agaaatattt|gaagaacccg|attacatgga ttggattagt|5400|
|tcttgtggtt|acgtggtttt|taactaaaag|tagtgaattt|ttgattttgg tgtgtgtgt|5460|
|cttgttgtta|gtatttgcta|gtcaaagtga|ttaaata|5497|

<210> SEQ ID NO 3
<211> LENGTH: 8241
<212> TYPE: DNA
<213> ORGANISM: Artificial Sequence
<220> FEATURE:
<223> OTHER INFORMATION: Synthetic

<400> SEQUENCE: 3

| | | | | |
|---|---|---|---|---|
|agatctaaca|tccaaagacg|aaaggttgaa|tgaaaccttt|ttgccatccg acatccacag|60|
|gtccattctc|acacataagt|gccaaacgca|acaggagggg|atacactagc agcagaccgt|120|
|tgcaaacgca|ggacctccac|tcctcttctc|ctcaacaccc|acttttgcca tcgaaaaacc|180|
|agcccagtta|ttgggcttga|ttggagctcg|ctcattccaa|ttccttctat taggctacta|240|
|acaccatgac|tttattagcc|tgtctatcct|ggccccctg|gcgaggttca tgtttgttta|300|
|tttccgaatg|caacaagctc|cgcattacac|ccgaacatca|ctccagatga gggctttctg|360|
|agtgtgggt|caaatagttt|catgttcccc|aaatggccca aaactgacag tttaaacgct|420|
|gtcttggaac|ctaatatgac|aaaagcgtga|tctcatccaa|gatgaactaa gtttggttcg|480|
|ttgaaatgct|aacggccagt|tggtcaaaaa|gaaacttcca|aaagtcgcca taccgtttgt|540|

-continued

| | |
|---|---|
| cttgtttggt attgattgac gaatgctcaa aaataatctc attaatgctt agcgcagtct | 600 |
| ctctatcgct tctgaacccc ggtgcacctg tgccgaaacg caaatgggga aacacccgct | 660 |
| ttttggatga ttatgcattg tctccacatt gtatgcttcc aagattctgg tgggaatact | 720 |
| gctgatagcc taacgttcat gatcaaaatt taactgttct aacccctact tgacagcaat | 780 |
| atataaacag aaggaagctg ccctgtctta aacctttttt tttatcatca ttattagctt | 840 |
| actttcataa ttgcgactgg ttccaattga caagcttttg attttaacga cttttaacga | 900 |
| caacttgaga agatcaaaaa acaactaatt attcgaagga tccaaacgat gagatttcct | 960 |
| tcaattttta ctgcagtttt attcgcagca tcctccgcat tagctgctcc agtcaacact | 1020 |
| acaacagaag atgaaacggc acaaattccg gctgaagctg tcatcggtta ctcagattta | 1080 |
| gaagggatt tcgatgttgc tgttttgcca ttttccaaca gcacaaataa cgggttattg | 1140 |
| tttataaata ctactattgc cagcattgct gctaaagaag aaggggtatc tctcgagaaa | 1200 |
| agagaggctg aagcccaggc ccaggcccag gcccaggccc aggaagaaac atgtatcatg | 1260 |
| gccccccggg agaggataaa ttgtggcttc cccggtgtca ccgcccagca gtgcacggag | 1320 |
| agaggttgct gttttgatga cagtgtccgg ggattcccgt ggtgcttcca ccccatggcc | 1380 |
| atcgagaaca ctcaagaaga agaatgtccc ttctaactag tggcgtagaa ttccctaggg | 1440 |
| cggccgcgaa ttaattcgcc ttagacatga ctgttcctca gttcaagttg gcacttacg | 1500 |
| agaagaccgg tcttgctaga ttctaatcaa gaggatgtca gaatgccatt tgcctgagag | 1560 |
| atgcaggctt catttttgat acttttttat ttgtaaccta tatagtatag gatttttttt | 1620 |
| gtcattttgt ttcttctcgt acgagcttgc tcctgatcag cctatctcgc agctgatgaa | 1680 |
| tatcttgtgg tagggttttg ggaaaatcat tcgagtttga tgttttttctt ggtatttccc | 1740 |
| actcctcttc agagtacaga agattaagtg agaagttcgt ttgtgcaagc ttatcgataa | 1800 |
| gctttaatgc ggtagtttat cacagttaaa ttgctaacgc agtcaggcac cgtgtatgaa | 1860 |
| atctaacaat gcgctcatcg tcatcctcgg caccgtcacc ctggatgctg taggcatagg | 1920 |
| cttggttatg ccggtactgc cgggcctctt gcgggatatc gtccattccg acagcatcgc | 1980 |
| cagtcactat ggcgtgctgc tagcgctata tgcgttgatg caatttctat gcgcacccgt | 2040 |
| tctcggagca ctgtccgacc gctttggccg ccgcccagtc ctgctcgctt cgctacttgg | 2100 |
| agccactatc gactacgcga tcatggcgac cacacccgtc ctgtggatct atcgaatcta | 2160 |
| aatgtaagtt aaaatctcta ataattaaa taagtcccag tttctccata cgaaccttaa | 2220 |
| cagcattgcg gtgagcatct agaccttcaa cagcagccaa atccatcact gcttggccaa | 2280 |
| tatgtttcag tccctcagga gttacgtctt gtgaagtgat gaacttctgg aaggttgcag | 2340 |
| tgttaactcc gctgtattga cgggcatatc cgtacgttgg caaagtgtgg ttggtaccgg | 2400 |
| aggagtaatc tccacaactc tctggagagt aggcaccaac aaacacagat ccagcgtgtt | 2460 |
| gtacttgatc aacataagaa gaagcattct cgatttgcag gatcaagtgt tcaggagcgt | 2520 |
| actgattgga catttccaaa gcctgctcgt aggttgcaac cgatagggtt gtagagtgtg | 2580 |
| caatacactt gcgtacaatt tcaaccccttg gcaactgcac agcttggttg tgaacagcat | 2640 |
| cttcaattct ggcaagctcc ttgtctgtca tatcgacagc caacagaatc acctgggaat | 2700 |
| caataccatg ttcagcttga gacagaaggt ctgaggcaac gaaatctgga tcagcgtatt | 2760 |
| tatcagcaat aactagaact tcagaaggcc cagcaggcat gtcaatacta cacagggctg | 2820 |
| atgtgtcatt tgaaccatc atcttggcag cagtaacgaa ctggtttcct ggaccaaata | 2880 |
| ttttgtcaca cttaggaaca gtttctgttc cgtaagccat agcagctact gcctgggcgc | 2940 |

```
ctcctgctag cacgatacac ttagcaccaa ccttgtgggc aacgtagatg acttctgggg   3000
taagggtacc atccttctta ggtggagatg caaaaacaat ttctttgcaa ccagcaactt   3060
tggcaggaac acccagcatc agggaagtgg aaggcagaat tgcggttcca ccaggaatat   3120
agaggccaac tttctcaata ggtcttgcaa aacgagagca gactacacca gggcaagtct   3180
caacttgcaa cgtctccgtt agttgagctt catggaattt cctgacgtta tctatagaga   3240
gatcaatggc tctcttaacg ttatctggca attgcataag ttcctctggg aaaggagctt   3300
ctaacacagg tgtcttcaaa gcgactccat caaacttggc agttagttct aaaagggctt   3360
tgtcaccatt ttgacgaaca ttgtcgacaa ttggtttgac taattccata atctgttccg   3420
ttttctggat aggacgacga agggcatctt caatttcttg tgaggaggcc ttagaaacgt   3480
caattttgca caattcaata cgaccttcag aagggacttc tttaggtttg gattcttctt   3540
taggttgttc cttggtgtat cctggcttgg catctccttt ccttctagtg acctttaggg   3600
acttcatatc caggtttctc tccacctcgt ccaacgtcac accgtacttg gcacatctaa   3660
ctaatgcaaa ataaaataag tcagcacatt cccaggctat atcttccttg gatttagctt   3720
ctgcaagttc atcagcttcc tccctaattt tagcgttcaa caaaacttcg tcgtcaaata   3780
accgtttggt ataagaacct tctggagcat tgctcttacg atcccacaag gtggcttcca   3840
tggctctaag acccttgat tggccaaaac aggaagtgcg ttccaagtga cagaaaccaa   3900
cacctgtttg ttcaaccaca aatttcaagc agtctccatc acaatccaat tcgatccca   3960 gcaacttttg agttgctcca gatgtagcac ctttatacca caaaccgtga cgacgagatt   4020
ggtagactcc agtttgtgtc cttatagcct ccggaataga cttttttggac gagtacacca   4080 ggcccaacga gtaattagaa gagtcagcca ccaaagtagt gaatagacca tcggggcggt   4140
cagtagtcaa agacgccaac aaaatttcac tgacagggaa cttttttgaca tcttcagaaa   4200 gttcgtattc agtagtcaat tgccgagcat caataatggg gattatacca gaagcaacag   4260
tggaagtcac atctaccaac tttgcggtct cagaaaaagc ataaacagtt ctactaccgc   4320
cattagtgaa acttttcaaa tcgcccagtg agaagaaaa aggcacagcg atactagcat   4380
tagcgggcaa ggatgcaact ttatcaacca gggtcctata gataacccta gcgcctggga   4440
tcatcctttg acaactcttt tctgccaaat ctaggtccaa aatcacttca ttgataccat   4500
tattgtacaa cttgagcaag ttgtcgatca gctcctcaaa ttggtcctct gtaacggatg   4560
actcaacttg cacattaact tgaagctcag tcgattgagt gaacttgatc aggttgtgca   4620
gctggtcagc agcataggga aacacggctt ttcctaccaa actcaaggaa ttatcaaact   4680
ctgcaacact tgcgtatgca ggtagcaagg gaaatgtcat acttgaagtc ggacagtgag   4740
tgtagtcttg agaaattctg aagccgtatt tttattatca gtgagtcagt catcaggaga   4800
tcctctacgc cggacgcatc gtggccgacc tgcaggtcgg catcaccggc gccacaggtg   4860
cggttgctgg cgcctatatc gccgacatca ccgatgggga agatcgggct cgccacttcg   4920
ggctcatgag cgcttgtttc ggcgtgggta tggtggcagg ccccgtgcc ggggactgt   4980 tgggcgccat ctccttgcat gcaccattcc ttgcggcggc ggtgctcaac ggcctcaacc   5040
tactactggg ctgcttccta atgcaggagt cgcataaggg agagcgtcga gtatctatga   5100
ttggaagtat gggaatggtg atacccgcat tcttcagtgt cttgaggtct cctatcagat   5160
tatgcccaac taaagcaacc ggaggaggag atttcatggt aaatttctct gacttttggt   5220
catcagtaga ctcgaactgt gagactatct cggttatgac agcagaaatg tccttcttgg   5280
```

```
agacagtaaa tgaagtccca ccaataaaga atccttgtt atcaggaaca aacttcttgt    5340
ttcgaacttt ttcggtgcct tgaactataa aatgtagagt ggatatgtcg ggtaggaatg    5400
gagcgggcaa atgcttacct tctggacctt caagaggtat gtagggtttg tagatactga    5460
tgccaacttc agtgacaacg ttgctatttc gttcaaacca ttccgaatcc agagaaatca    5520
aagttgtttg tctactattg atccaagcca gtgcggtctt gaaactgaca atagtgtgct    5580
cgtgttttga ggtcatcttt gtatgaataa atctagtctt tgatctaaat aatcttgacg    5640
agccaaggcg ataaataccc aaatctaaaa ctcttttaaa acgttaaaag gacaagtatg    5700
tctgcctgta ttaaacccca aatcagctcg tagtctgatc ctcatcaact tgaggggcac    5760
tatcttgttt tagagaaatt tgcggagatg cgatatcgag aaaaaggtac gctgatttta    5820
aacgtgaaat ttatctcaag atctctgcct cgcgcgtttc ggtgatgacg gtgaaaacct    5880
ctgacacatg cagctcccgg agacggtcac agcttgtctg taagcggatg ccgggagcag    5940
acaagcccgt cagggcgcgt cagcgggtgt tggcgggtgt cggggcgcag ccatgaccca    6000
gtcacgtagc gatagcggag tgtatactgg cttaactatg cggcatcaga gcagattgta    6060
ctgagagtgc accatatgcg gtgtgaaata ccgcacagat gcgtaaggag aaaataccgc    6120
atcaggcgct cttccgcttc ctcgctcact gactcgctgc gctcggtcgt tcggctgcgg    6180
cgagcggtat cagctcactc aaaggcggta atacggttat ccacagaatc aggggataac    6240
gcaggaaaga acatgtgagc aaaaggccag caaaaggcca ggaaccgtaa aaaggccgcg    6300
ttgctggcgt ttttccatag gctccgcccc cctgacgagc atcacaaaaa tcgacgctca    6360
agtcagaggt ggcgaaaccc gacaggacta taaagatacc aggcgtttcc ccctggaagc    6420
tccctcgtgc gctctcctgt tccgaccctg ccgcttaccg gatacctgtc cgcctttctc    6480
ccttcgggaa gcgtggcgct ttctcatagc tcacgctgta ggtatctcag ttcggtgtag    6540
gtcgttcgct ccaagctggg ctgtgtgcac gaaccccccg ttcagcccga ccgctgcgcc    6600
ttatccggta actatcgtct tgagtccaac ccggtaagac acgacttatc gccactggca    6660
gcagccactg gtaacaggat tagcagagcg aggtatgtag gcggtgctac agagttcttg    6720
aagtggtggc ctaactacgg ctacactaga aggacagtat ttggtatctg cgctctgctg    6780
aagccagtta ccttcggaaa aagagttggt agctcttgat ccggcaaaca aaccaccgct    6840
ggtagcggtg gtttttttgt ttgcaagcag cagattacgc gcagaaaaaa aggatctcaa    6900
gaagatcctt tgatctttc tacgggtct gacgctcagt ggaacgaaaa ctcacgttaa    6960
gggattttgg tcatgagatt atcaaaaagg atcttcacct agatcctttt aaattaaaaa    7020
tgaagtttta aatcaatcta agtatatat gagtaaactt ggtctgacag ttaccaatgc    7080
ttaatcagtg aggcacctat ctcagcgatc tgtctatttc gttcatccat agttgcctga    7140
ctccccgtcg tgtagataac tacgatacgg gagggcttac catctggccc cagtgctgca    7200
atgataccgc gagacccacg ctcaccggct ccagatttat cagcaataaa ccagccagcc    7260
ggaagggccg agcgcagaag tggtcctgca actttatccg cctccatcca gtctattaat    7320 tgttgccgg aagctagagt aagtagttcg ccagttaata gtttgcgcaa cgttgttgcc    7380
attgctgcag gcatcgtggt gtcacgctcg tcgtttggta tggcttcatt cagctccggt    7440
tcccaacgat caaggcgagt tacatgatcc cccatgttgt gcaaaaaagc ggttagctcc    7500
ttcggtcctc cgatcgttgt cagaagtaag ttggccgcag tgttatcact catggttatg    7560
gcagcactgc ataattctct tactgtcatg ccatccgtaa gatgctttc tgtgactggt    7620 gagtactcaa ccaagtcatt ctgagaatag tgtatgcggc gaccgagttg ctcttgcccg    7680
```

```
gcgtcaacac gggataatac cgcgccacat agcagaactt taaaagtgct catcattgga    7740
aaacgttctt cggggcgaaa actctcaagg atcttaccgc tgttgagatc cagttcgatg    7800
taacccactc gtgcacccaa ctgatcttca gcatctttta ctttcaccag cgtttctggg    7860
tgagcaaaaa caggaaggca aaatgccgca aaaagggaa taagggcgac acggaaatgt     7920
tgaatactca tactcttcct ttttcaatat tattgaagca tttatcaggg ttattgtctc    7980
atgagcggat acatatttga atgtatttag aaaaataaac aataggggt tccgcgcaca     8040 tttccccgaa aagtgccacc tgacgtctaa gaaaccatta ttatcatgac attaacctat    8100
aaaaataggc gtatcacgag gccctttcgt cttcaagaat taattctcat gtttgacagc    8160
ttatcatcga taagctgact catgttggta ttgtgaaata gacgcagatc gggaacactg    8220
aaaaataaca gttattattc g                                              8241
```

<210> SEQ ID NO 4
<211> LENGTH: 17
<212> TYPE: DNA
<213> ORGANISM: Artificial Sequence
<220> FEATURE:
<223> OTHER INFORMATION: Synthetic

<400> SEQUENCE: 4
caggcccagc ccaggcc    17

<210> SEQ ID NO 5
<211> LENGTH: 31
<212> TYPE: DNA
<213> ORGANISM: Artificial Sequence
<220> FEATURE:
<223> OTHER INFORMATION: Synthetic

<400> SEQUENCE: 5
gcactagtta gaagggacat tcttcttctt g    31

DELIVERY OF TREFOIL PEPTIDES

CROSS REFERENCE TO RELATED APPLICATIONS

The present application is a § 371 national stage filing of PCT/EP00/06343, filed Jul. 5, 2000, which claims priority to EP 99870143.7 filed Jul. 5, 1999.

FIELD OF THE INVENTION

The present invention relates to the field of in vivo protein delivery systems. More particularly, the present invention relates to the secretion in vivo of trefoil peptides by microorganisms, preferably bacterial strains, preferably non-pathogenic strains, preferably non-invasive strains, preferably food grade strains, methods for delivering trefoil peptides using said systems and the use of said trefoil peptide expression systems for treatment of inflammatory disorders of the gastro-intestinal tract

DESCRIPTION OF RELATED ART

*Lactococcus lactis* is a Gram-positive non-pathogenic lactic acid bacterium which can survive in the intestine (Klijn et al., 1995). It is not certain whether *L. lactis* can also be metabolically active in all of these environments.

The expression of tetanus toxin fragment C by *Lactococcus lactis* in view of vaccination was described by Wells et al. (1993) and Robinson et al. (1997). Further, it was demonstrated that when preparations of *L. lactis* bacteria engineered to express either Interleukin-2 or Interleukin-6 together with tetanus toxin fragment C (TTFC) were administered intranasally to mice, more than 10 times more anti-TTFC was produced than after similar administration of strains expressing TTFC alone (International patent application published under WO 97/14806). These results prove the use of a cytokine-secreting, non-invasive experimental bacterial vaccine vector to enhance immune responses to a co-expressed antigen. Also an approach has been described to attach heterologous protein fragments in the cell wall and by this way display them at the *L. lactis* surface, possibly leading to more enhanced vaccination properties (WO 97 09437 Steidler, Remaut, Wells).

Trefoil peptides are secreted by epithelial mucus cells and are stable in an acid environment. These peptides contribute to the protection of the mucosa (formation of a gel over the epithelium) and are probably involved in the repair of damaged mucosa by stimulation of epithelial migration (Playford et al., 1996). The production of trefoil peptides increases locally in regions where damage occurs such as gastric ulcers and colitis (Wright et al., 1990). Babyatsky et al. (1996) have shown that the administration of recombinant trefoil peptides reduces the damage at those places. In contradiction with most other proteins that are important for the protection of the mucosa (such as epidermal growth factor), most studies have demonstrated that trefoil peptides cause little or no proliferation (Playford et al., 1996). Three members of this family of trefoil peptides have been identified in humans and originally designated: pS2 (breast cancer oestrogen inducible gene, O. Lefebvre, 1993), SP (spasmolytic peptide) and ITF (intestinal trefoil factor). In the present nomenclature pS2 is renamed as TFF1, SP as TFF2 and ITF as TFF3 (see e.g. Wong et al., 1999). This new nomenclature will be used throughout the present text.

In humans, mice and rat TFF1 and TFF2 are predominantly found in the stomach while TFF3 is predominantly found in the duodenum and colon. Wong et al. (1999) give a recent overview of trefoil peptides. The contents of this article are incorporated by reference in the present disclosure. TFF1 is thought to act through a cell surface receptor (Tan et al., 1997).

The use of trefoil proteins or peptides for treatment of disorders of and damage to the alimentary canal, including the mouth, oesophagus, stomach, and large and small intestine, as well as for the protection and treatment of tissues that lie outside the alimentary canal are described in WO 97/38712 and WO 92/14837. These proteins can be used either to treat lesions in these areas or to inhibit the formation of lesions. These lesions can be caused by: radiation therapy or chemotherapy for the treatment of cancer, any other drug including alcohol which damages the alimentary canal, accidental exposure to radiation or to a caustic substance, infection, a digestive disorder including but not limited to non-ulcer dyspepsia, gastritis, peptic or duodenal ulcer, gastric cancer, MALT lymphoma, Menetier's syndrome, gastro-oesophageal reflux disease, Crohn's disease, ulcerative colitis and acute colitis of chemical, bacterial or obscure origin. Trefoil peptides are particularly useful to treat acute colitis.

ITF has also been used in combination with EGF (epidermal growth factor) for treating gastro-intestinal tract ulcers. In vitro and in vivo experiments have shown that the wound healing activities of EGF are markedly increased by treatment of EGF in combination with ITF, without increasing the proliferative action of EGF (Chinery and Playford, 1995).

Inflammatory bowel disease is the group name for a range of gastro-intestinal inflammations. Belonging to this group are enteritis, colitis, inflammations of respectively the mucosa of the duodenum or the colon. Crohn's disease (enteritis regionalis) and ulcerative colitis (colitis ulcerosa) are closely related, chronic and spontaneously recurring diseases of the gastro-intestinal tract. These diseases are immunologically mediated and have environmental and genetic causes. Sartor (1995) describes the different aspects of inflammatory bowel disease. Crohn's disease has been particularly studied by for instance Herfath and Sartor, (1994), Cominelli et al. (1994), and MacDermott (1989).

The aim of the present invention is to provide a method for delivering trefoil peptides to treat gastro-intestinal disorders.

Another aim of the present invention is to provide a pharmaceutical composition for treating gastro-intestinal disorders.

The present invention relates more particularly to a microorganism delivering a trefoil peptide in vivo. Preferentially said microorganism is a bacterial strain, preferably a non-pathogenic strain, preferably a non-invasive strain, preferably a food grade strain, more preferably a gram-positive bacterial strain, most preferably a lactic acid fermenting bacterial strain, preferably a *Lactococcus* or a *Lactobacillus* species expressing a trefoil peptide in vivo. The present invention is thus applicable to any of the *Lactococcus* or *Lactobacillus* species or subspecies selected from the list comprising *Lactococcus garvieae, Lactococcus lactis, Lactococcus lactis* subsp. *cremoris, Lactococcus lactis* subsp. *hordniae, Lactococcus lactis, Lactococcus lactis* subsp. *Lactis, Lactococcus piscium, Lactococcus plantarum, Lactococcus raffinolactis, Lactobacillus acetotolerans, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarius, Lactobacillus* aviarius subsp. araffinosus, Lactobacillus aviarius subsp. aviarius, Lactobacillus bavaricus, Lactobacillus bifermentans, Lactobacillus brevis, Lactobacillus buchneri, Lactobacillus bulgaricus, Lactobacillus carnis, Lactobacillus casei, Lactobacillus casei subsp. alactosus, Lactobacillus casei subsp. casei, Lactobacillus casei subsp. pseudoplantarum, Lactobacillus casei subsp. rhamnosus, Lactobacillus casei subsp. tolerans, Lactobacillus catenaformis, Lactobacillus cellobiosus, Lactobacillus collinoides, Lactobacillus confusus, Lactobacillus coryniformis, Lactobacillus coryniformis subsp. coryniformis, Lactobacillus coryniformis subsp. torquens, Lactobacillus crispatus, Lactobacillus curvatus, Lactobacillus curvatus subsp. curvatus, Lactobacillus curvatus subsp. melibiosus, Lactobacillus delbrueckii, Lactobacillus delbrueckii subsp. bulgaricus, Lactobacillus delbrueckii subsp. delbrueckii, Lactobacillus delbrueckii subsp. lactis, Lactobacillus divergens, Lactobacillus farciminis, Lactobacillus fermentum, Lactobacillus fornicalis, Lactobacillus fructivorans, Lactobacillus fructosus, Lactobacillus gallinarum, Lactobacillus gasseri, Lactobacillus graminis, Lactobacillus halotolerans, Lactobacillus hamsteri, Lactobacillus helveticus, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefiranofaciens, Lactobacillus kefirgranum, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus paracasei subsp. paracasei, Lactobacillus paracasei subsp. tolerans, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus reuteri, Lactobacillus rhamnosus, Lactobacillus rimae, Lactobacillus rogosae, Lactobacillus ruminis, Lactobacillus sakei, Lactobacillus sakei subsp. carnosus, Lactobacillus sakei subsp. sakei, Lactobacillus salivarius, Lactobacillus salivarius subsp. salicinius, Lactobacillus salivarius subsp. salivarius, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis, Lactobacillus yamanashiensis subsp. mali, Lactobacillus yamanashiensis subsp. Yamanashiensis and Lactobacillus zeae.

It was not obvious from the capacity of Lactococcus lactis to deliver one heterologous antigen or its ability to produce molecules such as IL-2 and IL-6 in vitro and in vivo that bacteria would be an appropriate vehicle for delivery of other types of peptides or polypeptides in vivo. Further it is unknown whether said trefoil peptides expressed by said bacterial strains will provide a beneficial effect to inflammatory diseases of the gastro-intestinal tract, such as inflammatory bowel disease or acute colitis.

It is, therefore, surprising that it could be demonstrated in the present Examples section that bacterial strains are able to express trefoil peptides in vivo when present in the gastrointestinal canal and exert a healing effect in acute colitis situations. By way of example, PCR fragments containing the coding region mouse TFF1 were cloned. Recombinant vectors comprising these PCR clones under the control of a promotor and the usp45 Lactococcus lactis secretion signal sequence were constructed. Transformed Lactococcus lactis strains were constructed which express mouse TFF1 trefoil peptides. It was further shown in an in vivo mice model system that recombinant mTFF1 produced by these bacteria can surprisingly exert healing effects on the distal part of the inflamed colon.

SUMMARY OF THE INVENTION

According to a preferred embodiment, the present invention relates particularly to a bacterial strain delivering trefoil peptide in vivo.

According to another preferred embodiment, the present invention relates to a bacterium delivering TFF1 in vivo.

It is to be understood that the present invention also relates to parts or variants of any trefoil peptide. Said parts refer to biologically active parts which can be generated by methods known to those skilled in the art. These parts will generally contain at least 10 contiguous amino acids, typically at least 20 contiguous amino acids, more typically at least 30 contiguous amino acids, usually at least 40 contiguous amino acids, and preferably at least 50 contiguous amino acids. Said variants refer to variants which have the same biological activity as the above mentioned trefoil peptides.

It should also be clear that bacterial strains according to the present invention as defined above, may also express additional recombinant proteins which are beneficial to the treatment of any envisaged disorder.

According to yet another embodiment, the present invention relates to a pharmaceutical composition comprising a microorganism expressing a trefoil peptide as defined above.

Advantageously, the pharmaceutical composition according to the present invention is preferably suitable for application to mucosal surfaces.

Pharmaceutical compositions according to the present invention, and for use in accordance to the present invention, may comprise, in addition to the microorganism, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration. Those of relevant skill in the art are well able to prepare suitable solutions.

According to another embodiment, the present invention relates to a method for the delivery of trefoil peptide to the gastro-intestinal tract comprising the administration of a microorganism as defined above.

According to another aspect, the present invention also relates to the use of a microorganism as defined above for the manufacture of an agent for the delivery of trefoil peptide to the gastro-intestinal tract.

According to another embodiment, the present invention relates to a method of treatment of gastric and/or intestinal diseases and/or disorders comprising administration of a microorganism as defined above.

The present invention also relates to a method of treatment of gastric and/or intestinal diseases and/or disorders comprising administration of a microorganism delivering a TFF1 trefoil peptide in vivo.

The trefoil proteins expressed by the bacterial strains according to the present invention can be used either to treat lesions in these areas or to inhibit the formation of lesions caused by gastro-intestinal diseases and disorders.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

FIGS. 2A–2B are the DNA sequence of plasmid pL2 mTFF1v1 (SEQ ID NO 1).

FIGS. 3A–3C are the DNA sequence of plasmid pT1mTFF1 (SEQ ID NO 2).

FIGS. 4A–4C are DNA sequence of plasmid pPICmTFF1 (SEQ ID NO 3).

DEFINITIONS

Figure 1A:
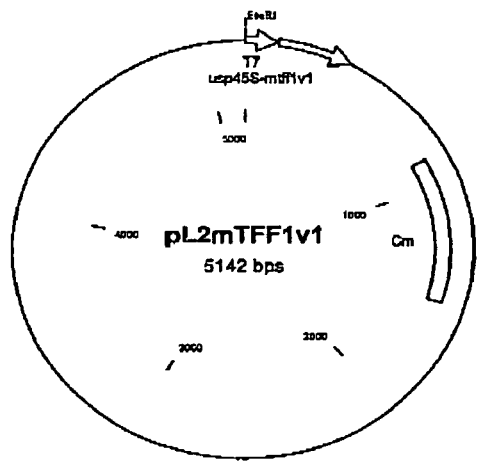
FIG. 1A is a schematic map of plasmids pL2 mTFF1v1. T7 is the major late promoter from coliphage T7 (Studier and Moffatt, 1986). P1 is the lactococcal promoter as in Waterfield et al., (1995), usp45S is a DNA fragment encoding the secretion signal peptide from the lactococal Usp45 protein (van Asseldonck et al., 1990), mtff1v1 is a DNA fragment encoding the mature part of murine TFF1, mtff1v1 is a DNA fragment encoding a truncated (missing two aminoterminal aa residues) mature murine TFF1, Cm is the chloramphenicol selection marker, Em is the erythromycin selection marker.

The expression "gastric and/or intestinal diseases and/or disorders" relates to all types of gastric, intestinal and gastro-intestinal diseases and/or disorders. In preferred embodiments of the invention this expression relates to acute gastro-intestinal inflammatory diseases and disorders. These diseases are preferably acute gastro-intestinal disorders of chemical, bacterial or obscure origin. Belonging to this group are enteritis, colitis, including but not limited to acute flare-ups in Crohn's disease and ulcerative colitis inflammations of, respectively, the mucosa of the duodenum or the colon. Also included herewith is traveller's disease. In other prefered embodiments of the invention the expression "gastric and/or intestinal diseases and/or disorders" relates to chronic and spontaneously recurring diseases of the gastro-intestinal tract such as Crohn's disease (enteritis regionalis) and ulcerative colitis (colitis ulcerosa).

The expression "gastric and/or intestinal diseases and/or disorders" also relates to diseases involving lesions at mucosal surfaces. As such, the disease states to be treated by the methods and pharmaceutical compositions of the invention can also include disorders of and damage to the alimentary canal, including the mouth, oesophagus, stomach, and large and small intestine, as well as for the protection and treatment of tissues that lie outside the alimentary canal. These lesions can be caused by: radiation therapy or chemotherapy for the treatment of cancer, any other drug including alcohol which damages the alimentary canal, accidental exposure to radiation or to a caustic substance, infection, a digestive disorder including but not limited to non-ulcer dyspepsia, gastritis, peptic or duodenal ulcer, gastric cancer, MALT lymphoma, Menetier's syndrome, gastro-oesophageal reflux disease, and Crohn's disease.

DETAILED DESCRIPTION OF THE INVENTION

The present invention thus relates to the use of a microorganism as described above for the preparation of a medicament for treatment of gastric and/or intestinal diseases and/or disorders.

The present invention also relates to the use of a microorganism as described above for the preparation of a medicament for treatment of acute gastro-intestinal inflammatory diseases, acute colitis, acute flare-ups of Crohn's diseases and ulcerative colitis, and for treatment of chronic and spontaneously recurring diseases of the gastro-intestinal tract comprising Crohn's disease (enteritis regionalis) and ulcerative colitis (colitis ulcerosa).

According to another embodiment, the invention relates to the use of a microorganism as described above for the preparation of a medicament for inhibiting the formation of lesions caused by gastric and/or intestinal diseases and disorders.

Administration of the microorganism may be orally or by means of any other method known in the art allowing the microorganism to enter the desired places to be treated, such as e.g. anal, vaginal. The microorganism may be applied in a nutrient medium, i.e. a medium containing a substance or substances which sustain (at least in vitro) metabolic activity of the microorganism. Such substances may sustain viability if not growth of the microorganism. Such substances may include an energy source such as glucose, amino acids and so on.

The individual to which the microorganism is administrated may be a human or an animal.

In a therapeutic context, i.e. where the biological effect of delivery of the polypeptide to an individual is beneficial to that individual, administration is preferably in a 'therapeutically effective amount', this being sufficient to show benefit to the patient. Such benefit may be at least amelioration of one symptom. The actual amount administered, and rate and time-course of administration, will depend on the aim of the administration, e.g. the biological effect sought in view of the nature and severity of the challenge and is the subject of routine optimisation. Prescriptions of treatment, for example decisions on dosage etc, is within the responsibility of general practitioners and other medical doctors.

A composition comprising microorganisms according to the present invention may be administered in accordance with the present invention alone or in combination with other treatments, either simultaneously or sequentially.

According to another embodiment, the present invention relates to a method for producing a microorganism delivering a trefoil peptide in vivo as defined above comprising transforming a microorganism with a recombinant vector carrying a trefoil polypeptide coding sequence under the control of a suitable promoter and a suitable bacterial secretion signal sequence.

Said bacterial secretion signal sequence can be any sequence known in the art to perform said function. Preferably, for L. lactis said secretion signal is the usp45 L. lactis secretion signal sequence. Said promoter sequence can be any promoter allowing expression of said coding sequence in said microorganism. Examples given in the examples section include the known inducible E. coli phage T7 promoter and the known constitutive P1 promoter of L. lactis.

The present invention also relates to a recombinant vector comprising at least a part of a trefoil peptide coding sequence under the control of a suitable promoter and a suitable secretion signal sequence. Said recombinant vector can be used to deliver in vivo at least a part of a trefoil peptide sequence which can exert on healing effect on damaged areas of the mucosal surfaces.

The present invention further relates to a recombinant vector as defined above, having a nucleotide sequence as represented by any of SEQ ID NOs 1, 2 or 4.

The following examples merely serve to illustrate the present invention, and are not to be construed as limiting the invention in any way. All documents mentioned in this text are incorporated by reference.

EXAMPLES

Example 1

Cloning and Expression of Mouse TTF1 (mTTF1)

Culture Media

GM17 is M17 (Difco, Detroit) supplemented with 0.5 w/v % of glucose. M9 medium contains per liter: 6 g of $Na_2HPO_4$, 3 g of $KH_2PO_4$, 1 g of $NH_4Cl$, 0.5 g of NaCl, 2 mmol of $MgSO_4$, 0.1 mmol of $CaCl_2$ and 5 g of Casitone (Difco). M9B is M9 supplemented with 2.1 g of $NaHCO_3$ and 2.65 g of $Na_2CO_3$ per liter. GM9B is M9B supplemented with 0.5 w/v % of glucose. LM9B is M9B supplemented with 0.5 w/v % of lactose.

When appropriate the antibiotics, erythromycin (Er) or chloramphenicol (Cm), were added to the respective media at final concentrations of 5 □g/ml each. The designation used to indicate the presence of antibiotic is, e.g. GM17Er, LM9BCm and so on. Solid media contained 1.2% agar.

Recombinant DNA Techniques

DNA modifying enzymes and restriction endonucleases were used under standard conditions and in the buffers recommended by the manufacturers. General molecular cloning techniques and the electrophoresis of DNA and proteins were carried out according to standard procedures. L. lactis was transformed by electroporation of cells grown in the presence of glycin (Wells et al., 1993a). Plasmid DNA was routinely purified using the QIAGEN® Plasmid Kit.

PCR Amplification of mTFF1

The PCR reaction was carried out on a plasmid containing mTFF1 cDNA (Lefebvre, 1993) using the oligonucleotide primers mTFF1S and mTFF1A. The mTFF1S primer corresponds to the first 18 nucleotides of the sense strand of mTFF1 from the first nucleotide behind the signal sequence. The mTFF1A primer is complementary to the last 26 nucleotides of the sense strand of mTFF1 including the stop codon, and introduces an extra SpeI restriction site.

```
mTFF1S: 5'-CAGGCCCAGCCCAGGCC -3' (SEQ ID NO 4)

mTFF1A: 5'-GCACTAGTTAGAAGGGACATTCTTCTTCTTG AG-3' (SEQ ID NO
5) wherein ACTAGT in mTFF1A represents an SpeI site.
```

PCR amplification was carried out using VENT™ DNA polymerase (New England Biolabs, Beverly, USA) which gives a PCR product carrying blunt ends. The PCR mixture consisted of 2 units Vent DNA polymerase, 10 μl VENT buffer (thermopol), 4 μl dXTP's (0.5 mM maximum), 5 μl (0.5 μM) of each primer, 1 μl (50 ng) template DNA and 74 μl $H_2O$. Six reactions were set up differing in their final concentration of $MgSO_4$, adjusted to 0, 1, 2, 3, 4 and 5 mM respectively. PCR amplification cycles were: $T_0$ for 300" at 94° C., $T_1$ for 45" at 94° C., $T_2$ for 30" at 60° C., $T_3$ for 20" at 72° C., $T_4$ for 10" at 20° C. These cycles $T_1$ until $T_3$ were carried out 30 times.

PCR amplification with these primers rendered the gene for mature mTFF1 lacking the signal sequence and including an additional SpeI restriction site. After checking by gel electrophoresis, the amplified fragment appeared as a band in the expected length range. The 5' end of the mTFF1 sequence contains two possible target sequences complementary to the forward primer. As a consequence two fragments of 202 base pairs and 208 base pairs respectively can be amplified from the mTFF1 cDNA by use of the mentioned primers. These fragments are not expected to be resolved by agarose gel electrophoresis.

Construction of Plasmids

Two different types of vectors were used as acceptors for the mTFF1 trefoil peptide encoding PCR fragment. The primary structure of the two parental vectors—pT1NX, derived from pTREX1 (Wells and Schofield, 1996), and pLET2NX, derived from pLET2N (Steidler et al., 1995)— contains the following common elements: a promoter (T7 or P1), the *L. lactis* usp45 secretion signal sequence (van Asseldonk et al., 1990 and European patent application published under No. 0 455 280), modified to contain a NaeI restriction site overlapping the sequence encoding the ultimate aa residue (Steidler et al., 1995), and a downstream SpeI restriction site. pT1NX derived plasmids specify resistance to erythromycin; pLET2NX derived plasmids specify resistance to chloramphenicol. The PCR fragments were treated for 1 hour at 37° C. using 50 µl DNA solution, 10 µl SpeI-buffer, 50 units SpeI, 10 units T4 polynucleotide kinase (Gibco BRL, Bethesda, USA), 0.5 mM ATP, adjusted to pH 7.5, and 36 µl H$_2$O. The vector pT1NX was digested for 1 hour at 37° C. using 10 á 20 µl purified DNA, 10 µl NaeI buffer, 10 units NaeI, 50 units SpeI, 1 unit calf intestine alkaline phosphatase (Boehringer, Mannheim, Germany) and 73 á 63 µl H$_2$O. After 30 minutes incubation, 50 units of SpeI and 10 units of NaeI were again added to the mixture. The restriction enzymes were inactivated and extracted from the mixture by phenol/chloroform extraction. After restriction digestion, the mTFF1-derived band (comprising a 195 bp and a 201 bp fragment as described before under "PCR amplification of mouse TFF1 (mTFF1)", and the vector parts were excised from the agarose gel. Following ligation of the respective PCR fragments and the vector for 45 minutes at 16° C. using "Ready To Go" T4 DNA ligase (Pharmacia Biotech, UK) recombinant plasmids were obtained containing the mTFF1 cistron as an in-frame fusion to the usp45 secretion signal sequence under the control of the promoter.

Figure 1B:
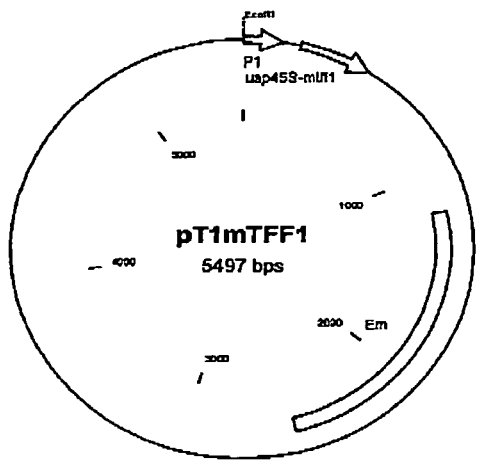
FIG. 1B is a schematic map of plasmid pT1mTFF1.

The plasmid pT1mTFF1 (FIG. 1B), which contains the constitutive *L. lactis* P1 promoter, resulted from ligation of the purified NaeI-SpeI vector part of pT1NX and the SpeI cut and 5' phosphorylated PCR fragment.

The plasmid pL2 mTFF1v1 (FIG. 1A), which contains the inducible *E. coli* phage T7 promoter, resulted from ligation of the purified NaeI-SpeI vector part of pLET2N and the SpeI cut and 5' phosphorylated PCR fragment. The T7 promoter can only be activated by the cognate T7 RNA polymerase encoded by e.g. plasmid pILPOL. This plasmid is present in *L. lactis* strain MG1820 [pILPOL] (Wells et al., 1993c).

For structural analysis plasmid pT1mTFF1 was transformed into *L. lactis* strain MG1363. The cells were grown on GM17Er plates. Colonies were grown in 2.5 ml GM17Er and the plasmid was isolated. By means of an analytical digest, the restriction pattern of the pT1NX vector (2 µl DNA (pT1NX), 20 units EcoRI, 50 units SpeI, 2 µl SpeI-buffer and 15 µl H$_2$O) and the isolated recombinant plasmid (5 µl DNA, 20 units EcoRI, 50 units SpeI, 2 µl SpeI-buffer, 0.25 µl of a 10 µg/ml Rnase A stock solution, 12 µl H$_2$O) were compared. The plasmids were cut with EcoRI and SpeI for 1 h at 37° C. In the reference plasmids, two linear fragments of 907 bp and 4999 bp are predicted. In pT1mTFF 1, two bands of 499 bp and 4999 bp are predicted. The sizes of the experimentally obtained fragments, as visualized by agarose gel electrophoresis and EtBr staining, were consistent with the predicted lengths. From each recombinant plasmid, one positive culture was streaked out on GM17Er plates to obtain isolated colonies. One colony was subsequently inoculated in 100 ml GM17Er medium and grown to saturation. The cells were collected and the plasmids were purified. Their physical structure was verified by restriction enzyme analysis and agarose gel electrophoresis. In addition, sequence analysis revealed that the mTFF1 cistron had been ligated perfectly in frame with the usp45 secretion leader sequence. pT1 mTFF1 contains a 208 bp insert which represents the complete coding sequence of mature mTFF1 (as described before under "PCR amplification of mouse TFF1 (mTFF1)").

For structural analysis plasmids pL2mTFF1v1 was transformed into strain MG1820[pILPOL]. The cells were grown on GM17Cm plates. Colonies were grown in 2.5 ml GM17Cm and the plasmids were isolated. By means of an analytical digest, the restriction pattern of the pLET2NX vector (2 µl DNA (pLET2NX), 20 units EcoRI, 50 units SpeI, 2 µl SpeI-buffer and 15 µl H$_2$O) and the isolated recombinant plasmid (5 µl DNA, 20 units EcoRI, 50 units SpeI, 2 µl SpeI-buffer, 0.25 µl of a 10 µg/ml Rnase A stock solution, 12 µl H$_2$O) were compared. The recombinant plasmid was cut with EcoRI and SpeI for 1 h at 37° C. In the reference plasmids, two linear fragments of 907 bp and 4650 bp are predicted. In pL2 mTFF1, two bands of 499 bp and 4650 bp are predicted. The sizes of the experimentally obtained fragments, as visualized by agarose gel electrophoresis and EtBr staining, were consistent with the predicted lengths. From the recombinant plasmid, one positive culture was streaked out on GM17Cm plates to obtain isolated colonies. One colony was subsequently inoculated in 100 ml GM17Cm medium and grown to saturation. The cells were collected and the plasmid was purified. Its physical structure was verified by restriction enzyme analysis and agarose gel electrophoresis. In addition, sequence analysis revealed that the mTFF1 cistron had been ligated in frame with the usp45 secretion leader sequence. The analysis further showed that pL2 mTFF1v1 contains a 202 bp insert (consequently missing the first two aminoterminal aa residues of mature mTFF1; as described before under "PCR amplification of mouse TFF1 (mTFF1)"). The sequences of the recombinant plasmids are given in FIGS. 2A–2B and 3A–3C. Their complete sequences were compiled from the published sequences of the constituting parts. In addition, relevant sections of the sequences such as PCR fragments and ligation junction points were experimentally verified.

Protein Expression in Transformed *L. lactis*

*L. lactis* strains were transformed with the plasmids as constructed above. For transformation of the pT1mTFF1 plasmid, *L. lactis* strain MG1363 (Gasson, 1983) was used. For transformation of the pL2mTFF1v1 plasmid, *L. lactis* strain MG1820 (pILPOL) (Maeda and Gasson, 1986) was used.

The expression of the proteins by these transformed *L. lactis* strains was detected by SDS-PAGE.

To prepare culture supernatant fractions, the cells were grown for 20 hours at 28° C. in five ml GM17Er medium for the pT1mTFF1 plasmid or GM17Cm medium for the pL2mTFF1v1 plasmid. The cultures were diluted 1/100 in five ml of either GM17Er or GM17Cm medium and grown for 3 hours at 28° C. The cells were collected by centrifugation at 2800 rpm for 20 min and resuspended in five ml of the appropriate medium, i.e., GM9BEr for MG1363 cells or LM9BCm for MG1820 [PILPOL] cells. After a further five hours of growth the cells were pelleted. The proteins present in the medium fractions were recovered by phenol extraction and ethanol precipitation.

Figure 5:
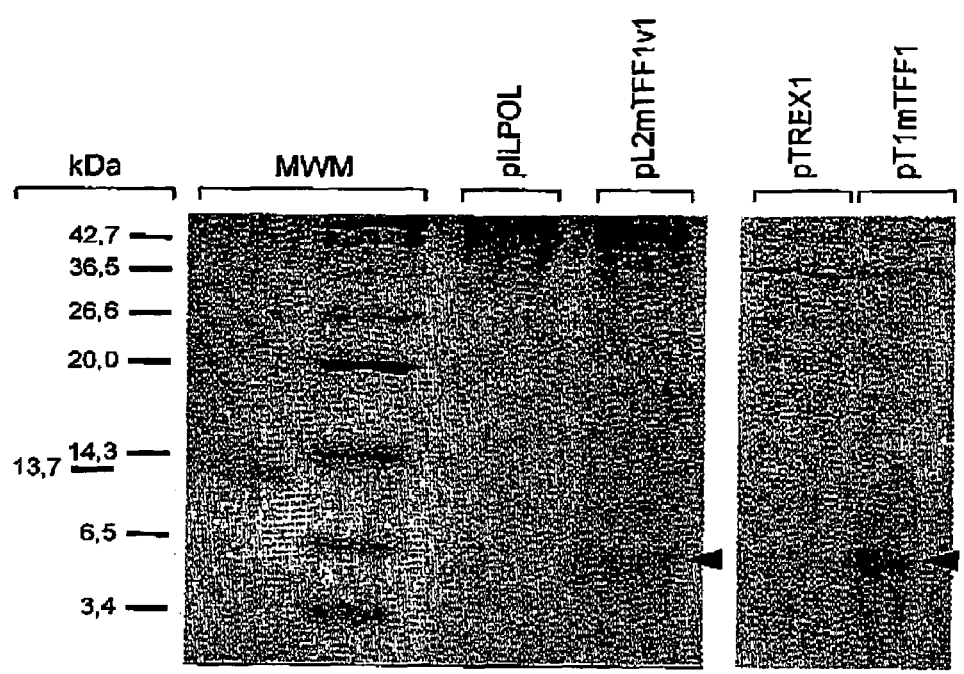
FIG. 5 is an SDS-PAGE. The different protein fractions are derived from the medium of *L. lactis* MG1820 [pILPOL] (control), MG1820 [pILPOL; pL2mTFF1v1], MG1363 [pTREX1] or MG1363 [pT1mTFF1] cells. The two left lanes contain marker proteins wherein the molecular weight is given in kDa. The proteins were visualised using Coomassie Blue® staining.

The proteins expressed in the culture supernatant fraction of a *L. lactis* MG1820 control strain compared to *L. lactis* MG1820 strains transformed with [pILPOL; pL2 mTFF1v1] and *L. lactis* MG1363 transformed with [pTREX1; pT1mTFF1] are shown in FIG. 5. This figure shows an extra protein band of the appropriate size (indicated by the arrowhead) in MG1820 [pL2mTFF1v1] and MG1363 [pT1mTFF1] when compared with the controls. As can be observed from this figure, the expression of the recombinant gene is quite low. This renders the observed in vivo result surprising since others use purified trefoil peptides in therapies for the repair of gastric and intestinal injury at dramatically higher levels; e.g. Tran et al. (1999) used daily intrarectal application of human recombinant TTF2 at levels of 2.5 mg/kg body weight for five days to obtain a reduction in the inflammatory index of experimentally installed colitis in rats (intracolonic administration of dinitrobenzene sulphonic acid in alcohol).

Example 2

In Vivo Testing of MG1363 [pT1mTFF1]

Preparation of Cells for Intragastric Administration

Transformants of *L. lactis* strains, MG1363 [pTREX1], MG1363 [pT1mTFF1] were streaked on GM17Er plates and grown overnight at 28° C. In each case a single colony was subsequently grown overnight at 28° C. in 15 ml GM17Er medium. To this culture, 15 ml 100% glycerol was added in order to preserve said cells at −20° C. Each day, the necessary amount of cells could be inoculated for treatment of mice. To this end the culture was diluted 1/200 into 10 ml GM17Er medium. After minimum 20 hours of growth at 30° C., the cells were collected by centrifugation for 15 min at 2800 rpm. The cells were then resuspended in 1 ml M9B without antibiotic.

In Vivo Tests in Mice with Acute Colitis

The effect of the trefoil peptides expressed from these *L. lactis* bacteria was tested out in mice suffering from acute colitis. Twenty-one female Balb/c mice received 5% DSS (dextrane sodium sulphate) dissolved in their drinking water during 7 days. In this manner, acute colitis was induced (Kojouharoff et al., 1997). For therapeutic purposes these mice were orally inoculated daily by means of a gastric catheter using 100 µl bacterial suspension (minimum $1.10^8$ cells) from day 1 until day 7 of the DSS treatment. As indicated Six mice were inoculated with MG1363 [pTREX1] cells, six mice were inoculated with MG1363 [pT1mTFF1] cells and three mice were not inoculated (DSS control). On day 8 after the induction of colitis, the mice were sacrificed and examined immunologically and histologically.

Immunological testing of the sera showed that the treated mice did not show an immune response towards the expressed proteins. Serum was taken from the mice which were bled at day 8. This serum was analysed via Western blotting to check whether it contained antibodies against the proteins present in the medium fractions of the *L. lactis* cells. The medium fractions used were derived from the *L. lactis* strains MG1363 [pTREX1] and MG1363 [pT1mTFF1]. An equivalent of 1 ml of concentrated (phenol extraction and ethanol precipitation) medium fractions were analysed by SDS-polyacrylamide (20%) gel electrophoresis. After blotting to nitrocellulose filters, the filters were incubated for 1 hour with the serum solutions of the 4 groups of mice. The serum was diluted 500 times in 20 ml nitrocellulose blocking buffer BLOTTO®: 100 ml 10× PBS, 150 ml 1M NaCl, 2 ml TRITON X-100®, 25 g fat-free milkpowder, water up to a total volume of 1 liter). As a secondary antibody, sheep anti-mouse IgG coupled to horseradish peroxidase (HRP) was used. Using the 500 times diluted serum, no signal was detected.

Histological analysis was performed on colons of the treated mice. The colons were cut in the length direction and divided in three equal portions: the distal (nearest to the anus), middle and proximal parts. These colon parts were analysed histologically after an overnight fixation in 3.7% formaldehyde (in PBS), followed by paraffin embedding, ensuring upright positioning of the tissue samples in the paraffin blocks. Of each tissue sample, three parallel 3 µm thick longitudinal sections, evenly spaced over the sample, were made. These crossections were coloured with hematoxylin/eosin. Histological analysis was performed in a blind fashion, meaning that the labels on the slides were covered before scoring the sections. Slides carrying sections obtained from the several groups of mice were randomized before microscopic examination. Each slide was then assigned a histological score (ranging from 0 to 5) according to the symptomatic description as defined in Table 1.

TABLE 1

Symptomatic description of histological scores.

| Score | Epithelium damage | Inflammatory infiltration* |
|---|---|---|
| 0 | Normal morphology | No infiltration |
| 1 | Loss of a few goblet cells | Infiltration around the basis of the crypts |
| 2 | Widespread loss of goblet cells | Infiltration which reaches the Lamina muscularis mucosae |
| 3 | Loss of crypts | Extensive infiltration which reaches the Lamina muscularis mucosae and thickening of the mucosa with prominent oedema |
| 4 | Widespread loss of crypts | Infiltration which reaches the Lamina submucosa |

*Inflammatory infiltration includes infiltration of the granulocytes, macrophages and lymphocytes.

For each mouse and for each colon part, the average score of the three sections was calculated. In the distal and middle parts of the colon, the inflammation consisting of epithelial damage and infiltration were the most pronounced. In the proximal part, almost no inflammation could be observed. The average histological score was calculated for both the distal and the middle colon part per group of animals. The final histological sum score is the sum of the two separate scores (sum score=score of epithelial damage+score of infiltration) and is a measure for the degree of the inflammation. The histological sum scores of the distal colon part for each of the groups of mice is shown in FIGS. 6A–6C.

Figure 6A:
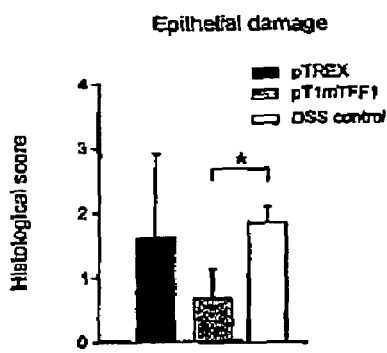
FIG. 6A is a representation of the histological scores of the distal part of the colon, showing epithelium damage (distal part colon).
Figure 6B:
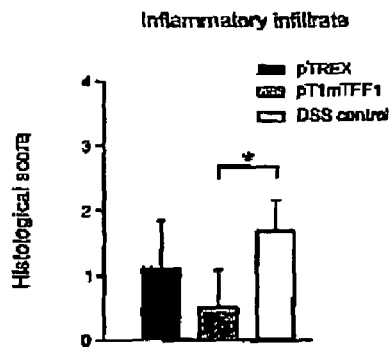
FIG. 6B is a representation of the histological scores of the distal part of the colon, showing inflammatory infiltration (distal part colon).
Figure 6C:
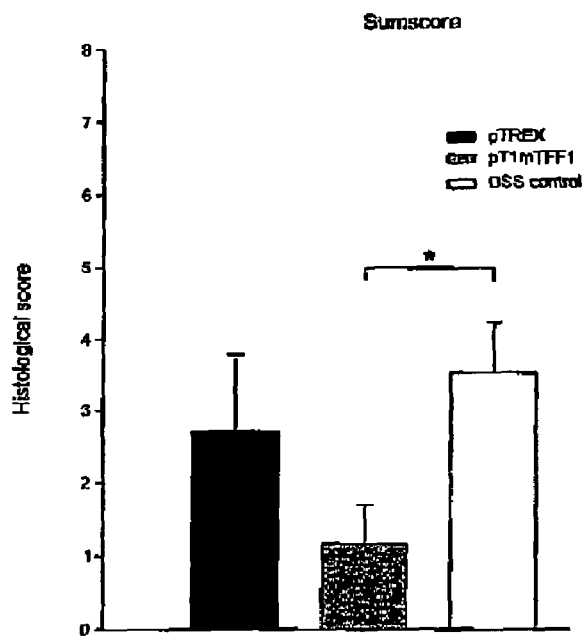
FIG. 6C is a representation of the histological scores of the distal part of the colon, showing the sum of the histological scores of the top graphics (distal part colon).

From the histological scores for the distal part of the colon as set out in FIGS. 6A–6C, it could be concluded that there is a clear decrease of inflammation upon inoculation of mice with *L. lactis* cells producing trefoil peptides. Mice having received [pT1mTFF1] transformed *L. lactis* cells show a significant reduction of the inflammation of more than 65%.

Figure 7:
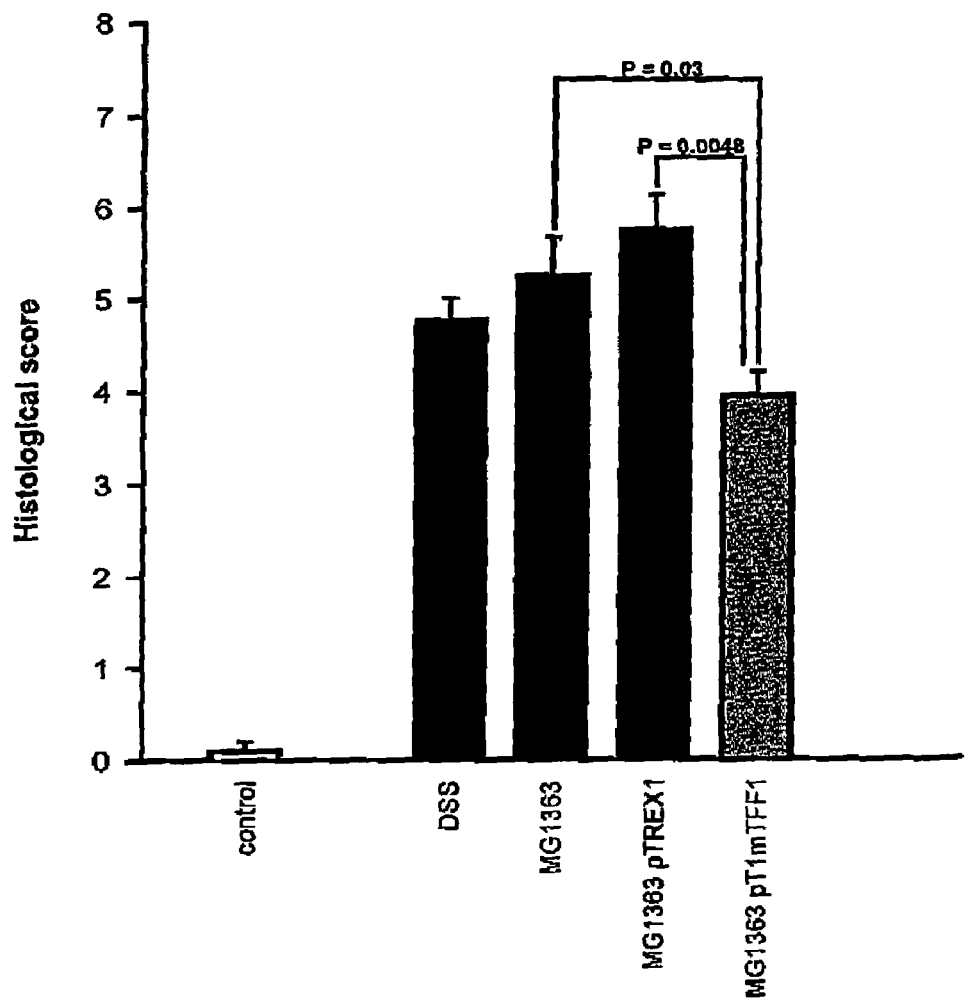
FIG. 7 is a representation of the histological scores of the distal part of the colon of healthy mice (control) or mice with acute DSS colitis without treatment (DSS) or after treatment wit MG1363, MG1363 [pTREX1] or MG1363 [pT1mTFF1] cells.

As can be seen from FIGS. 6A–6C, the inflammatory infiltration and the epithelial damage in the distal part of the colon are significantly decreased following inoculation with recombinant *L. lactis* strains which secrete mTFF1 polypeptide These results were confirmed in a separate experiment which was conducted equally, including larger groups (group size=10) and more control groups. FIG. 7 shows histological scores (obtained as described above) of healthy control mice (control) and of mice which received DSS as described, either left untreated (DSS) or treated (as described above) with MG1363, MG1363 [pT1TREX1] or MG1363 [pT1mTFF1] as indicated. The experiment shows a clear and significant decrease in the intestinal inflammation in the group of mice treated with MG1363 [pT1mTFF1]

Figure 8:
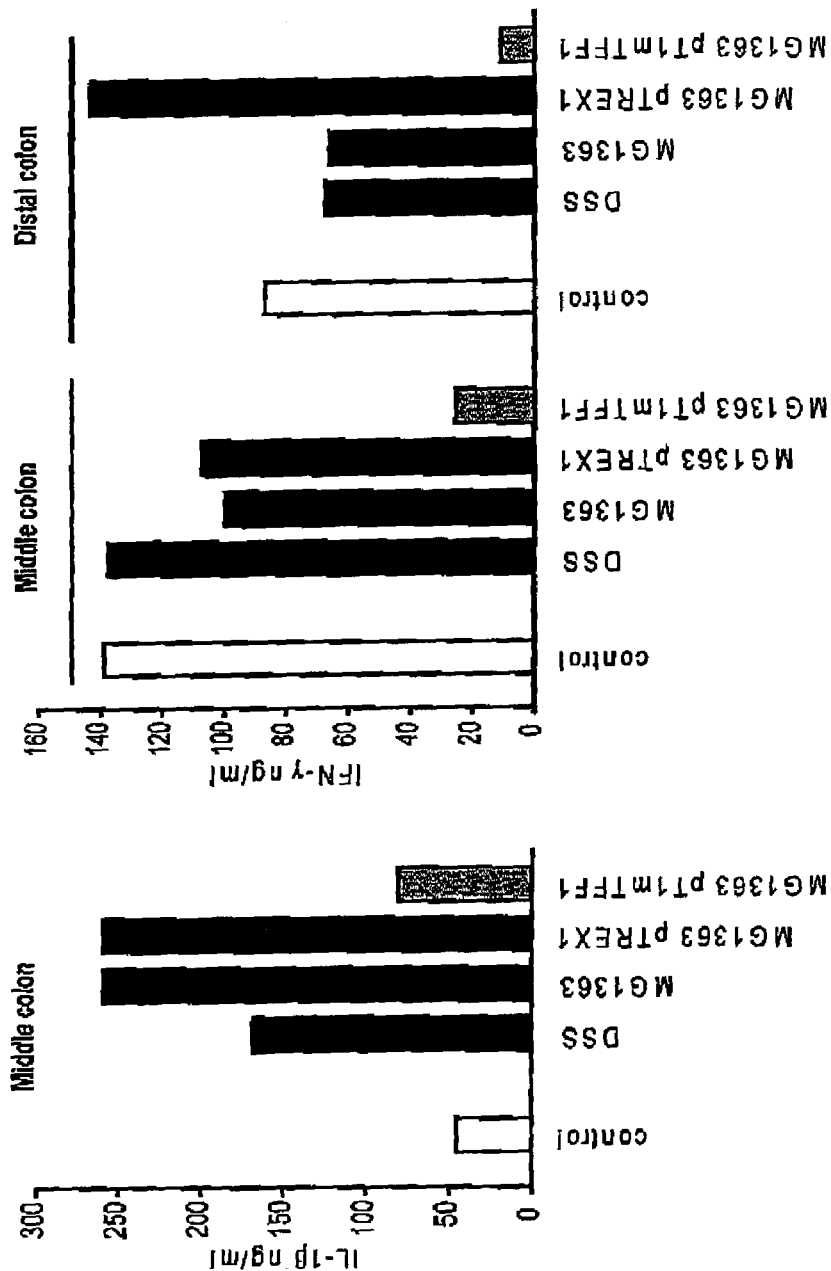
FIG. 8A shows pro-inflammatory cytokine titrations in acute inflamed colon tissue, specifically interleukin-1β in distal colon of healthy mice (control) or mice with acute DSS colitis without treatment (DSS) or after treatment wit MG1363, MG1363 [pTREX1] or MG1363 [pT1mTFF1] cells.
FIG. 8B shows pro-inflammatory cytokine titrations in acute inflamed colon tissue, specifically interferon-γ in middle and distal colon (right) of healthy mice (control) or mice with acute DSS colitis without treatment (DSS) or after treatment wit MG1363, MG1363 [pTREX1] or MG1363 [pT1mTFF1] cells.

The latter experiment was also evaluated by determining the levels of interleukin-1β (IL-1β) and interferon-γ (IFN-γ), both pro-inflammatory cytokines well known to the skilled. Mice (n=10) were inoculated with the strains indicated as described. Control=healthy mice, DSS=mice receiving 5% DSS in the drinking water without any treatment. The colon was prepared out and areas with equal surface were isolated by means of a punch (Ø=4 mm). The tissue samples of each group were overlayed with 500 μl RPMI+10% fetal calf serum and incubated overnight at 37° C. The supernatant was collected and titrated for cytokine content by ELISA. The amount of IL-1β and IFN-γ in the respective tissues is shown in FIGS. 8A–8B. The results show a clear reduction in these pro-inflammatory cytokines in groups of mice treated with MG1363 [pT1mTFF1].

Example 3

Comparison of Treatment with MG1363 [pT1TFF1] and Purified TFF1

Construction of Plasmids

Figure 1C:
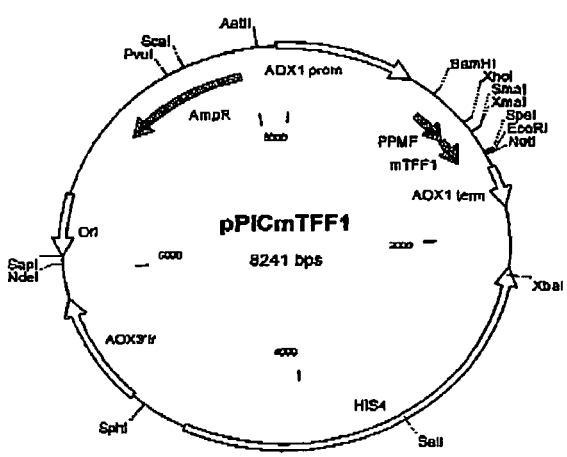
FIG. 1C is a schematic map of plasmid pPICmTFF1. PPMF is the prepro *Saccharomyces cerevisiae* α-mating factor; AOX1 prom is the alcohol oxidase promotor; AOX1 term is the alcohol oxidase terminator; HIS4 is the Histidol dehydrogenase gene; Ori is an *Escherichia coli* origin of replication; AOXfr is a 3' fragment of the alcohol oxidase gene; AmpR is the ampicilin resistance gene. All components are from the pPIC9 plasmid (Invitrogen).

For the expression of mTFF1 form *Pichia pastoris* we constructed the plasmid pPICmTFF1 (FIG. 1C). For this, the mTFF1 gene was PCR amplified as described (PCR amplification of mouse TFF1). This fragment was ligated in the opened NaeI restriction site of a derivative of pPIC9 (Invitrogen). The ligation mixture is transformed to *E. coli* MC1061 and correctly assembled clones were identified by restriction analysys and DNA sequencing (sequence as in FIGS. 4A–4C). In the resulting plasmid pPICmTFF1, the mTFF1 sequence is fused in frame with the *Sacharomuces cerevisiae* α-mating factor prepro secretion signal Expression and Purification of mTFF1

Figure 9:
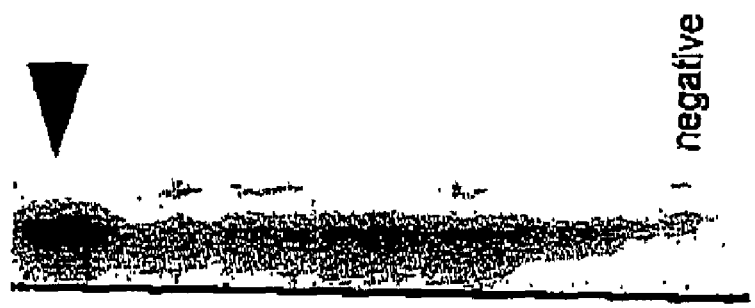
FIG. 9 is an SDS-PAGE of protein fractions from the medium of selected *Pichia pastoris* (GST115::pPICmTFF1) and negative control. The mTFF1 producer clone which was further used for production of mTFF1 is indicated by an arrowhead The proteins were visualised using Coomassie Blue® staining.

The plasmid pPICmFF1 was transferred to *Pichia pastoris* GST115 by a method as described in Logghe (1995) and positive clones, which had the mTFF1 unit integrated in the his4 locus, were selected by PCR identification. These positive clones were induced with methanol and screened for expression by protein analysis of culture supernatant and one clone which showed, when compared to the negative control (negative), a particularly high expression of an extra band at 6.5 kDa (GST115::pPICmTFF1) was retained for further work (FIG. 9, indicated by arrowhead). The extra protein band was identified as mTFF1 by protein sequencing. The expression procedure was optimised scaled up and optimised to a 16 l culture and mTFF1 was purified from the culture supernatant.

For this, methanol induced GST115::pPICmTFF1 supernatans was concentrated by tangential filtration (Millipore proflux M12, cut off 3000 Da) and was dialysed to pH 7.4 in a 0.02 M phosphate buffer. mTFF1 was purified from this concentrate on an ion-exchange column (Q-column of Biorad). The proteins were eluted form the column by an isocrational salt gradient. The resultant mTFF1 was more than 99% pure and was further concentrated. The final preparation contains less than 160 ng LPS/ml This amount of LPS is within acceptable limits and the pS2 protein can be used in future experiments.

Figure 10A:
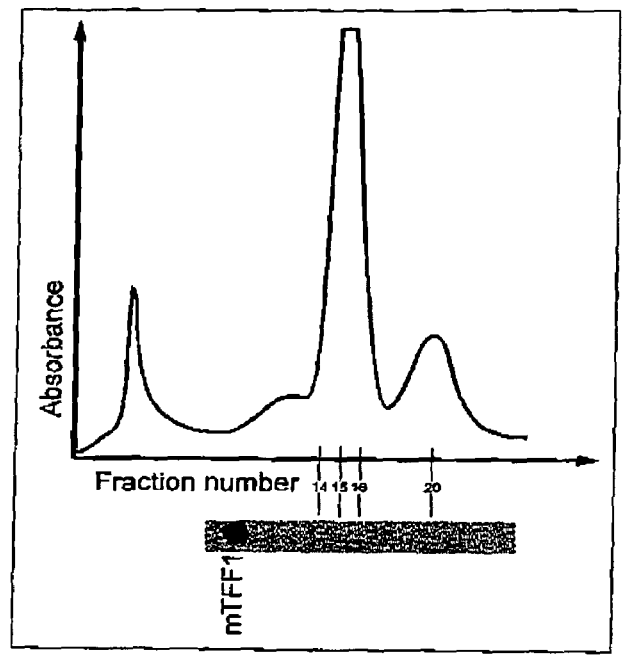
FIG. 10A is a Gelfiltration pattern of purified mTFF1 (SUPERDEX 75®; Pharmacia). The mTFF1 protein eluted in two peaks with the majority being present in fractions 14, 15, 16 (dimer) and 20 (monomer). The identity of the protein in these fractions was shown to be mTFF1 by SDS-PAGE (insert). The proteins were visualised using Coomassie® Blue staining.
Figure 10B:
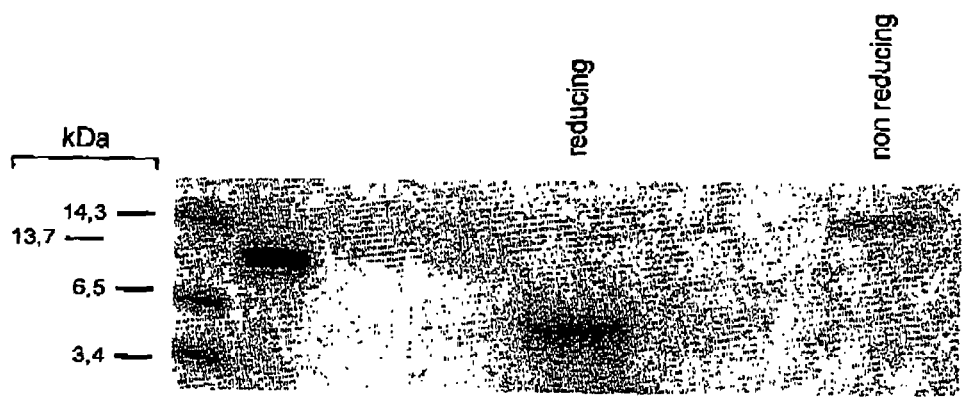
FIG. 10B illustrates reducing and non reducing SDS-PAGE of purified mTFF1. Left lanes are size markers of indicated sizes, Coomassie® brilliant blue staining.

Following analysis on a size exclusion column of purified mTFF1 (SUPERDEX 75®; Pharmacia) we conclude that 7.5% of the mTFF1 is in the monomeric form, and 92.5% is in the dimeric form (FIG. 10A). This was confirmed by reducing versus non reducing SDS-PAGE of the purified mTFF1 (FIG. 10B).

Assessment of Biological Activity of Purified TFF1

A well know feature of TFF1 protein is that after administration of the protein to Caco-2 cell monolayers it significantly lowers the surface expression of E-cadherin (Liu et al., 1997). We showed a lowering of 10% of the E-cadherin surface expression after the above described preparation of mTFF1 was administred to Caco-2 monolayers.

Figure 11:
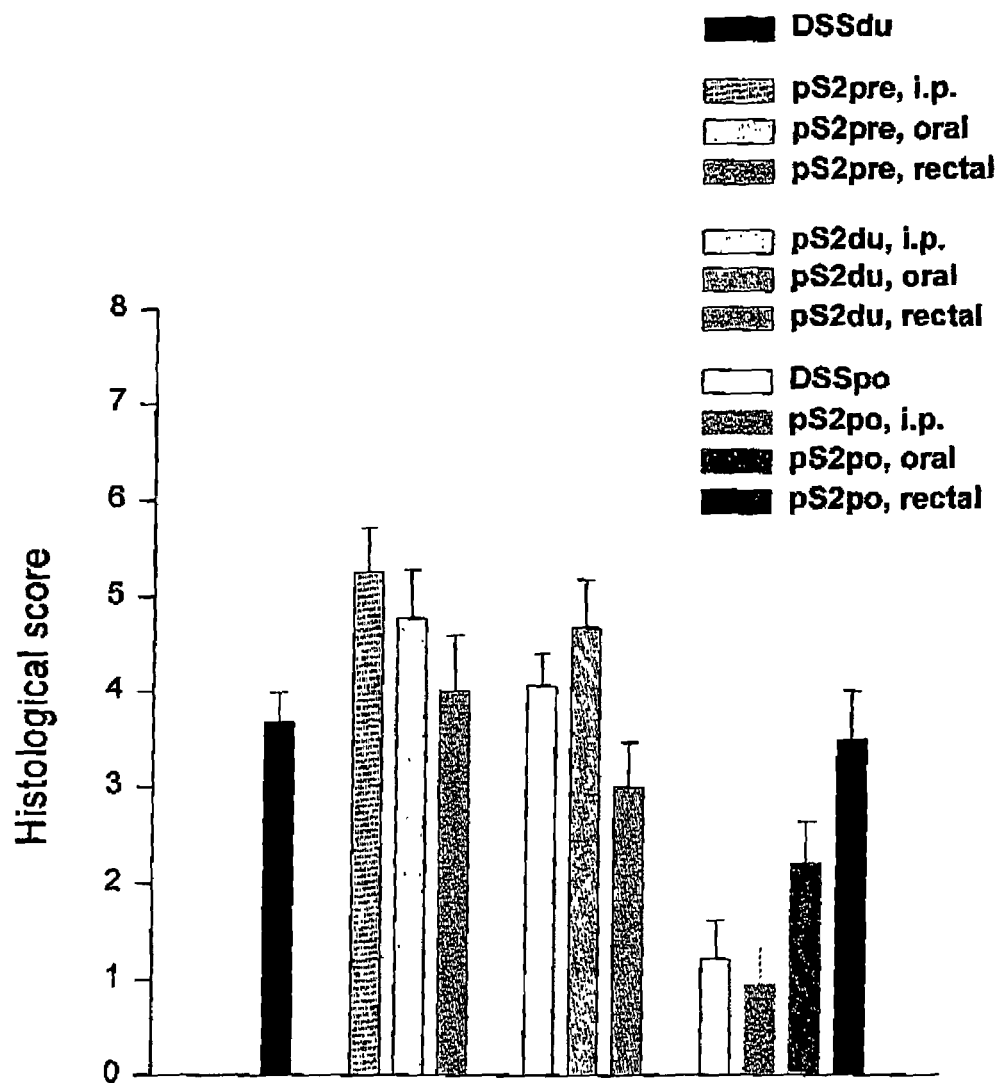
FIG. 11 is a representation of the histological scores of the distal part of the colon of mice treated by intraperitoneal injection (i.p.), oral (oral) and rectal (rectal) inoculation, before (pre), during (du) or after (po) installation of acute DSS-induced colitis. DSSdu represents scores of PBS treated mice induced for acute DSS colitis.

Treatment of Murine Acute Colitis with Purified mTFF1:

For induction of acute colitis mice received 6% dextran sulfate sodium (DSS, MW 40 000) dissolved in drinking water for 7 days (Kojouharoff et al., 1997). Mice used for experiments were age-matched and had received DSS treatment simultaneously. For therapeutic purposes, mice were treated daily with 50 μg mTFF1 in 200 μl PBS before DSS administration from day −7 to 0 (pre-treatment groups), during DSS administration from day 0 to 7 (during-treatment groups) and after DSS administration from day 7 to 14 (post-treatment groups). To study different routes to deliver mTFF1, mice were treated by intraperitoneal (i.p.) injection, intragastric inoculation and rectal administration in each setup. Mice were killed on day 8 after receiving drinking water without DSS for one day (pre-treatment and during-treatment groups) and on day 14 after receiving drinking water without DSS for seven days (post-treatment groups). Non-treated control groups with DSS in drinking water were killed on day 8 and day 14. All groups consisted of 9 mice. Results are represented in FIG. 11 and clearly show that in no treatment regime any statistically significant improvement can be observed. This renders the described invention surprising since a clear improvement has been observed (FIGS. 6A–6C and 7). This means that the delivery of TFF1 through *L. lactis* makes an essential contribution to the observed therapeutic effect.

REFERENCES

Babyatsky M. W., de Beaumont M., Thim L., Podolsky D. K. (1996). Oral trefoil peptides protect against ethanol- and indomethacin-induced gastric injury in rats. Gastroenterology 110, 489–497.

Chinery R. and Playford R. J. (1995). Combined intestinal trefoil factor and epidermal growth factor is prophylactic against indomethacin-induced gastric damage in the rat. Clinical Science 88, 401–403.

Cominelli F., Kam L., Casini-Raggi V. et al. (1994). Specific mucosal imbalance of IL-1 and IL-1 receptor antagonist (IL-1ra) in IBD: A potential mechanism of chronic inflammation. Gastroenterology 106, A667.

Gasson M. J. (1983). Plasmid complements of *Streptococcus lactis* NCDO 712 and other lactic streptococci after protoplast-induced curing. J. Bacteriol. 154, 1–9.

Herfarth H. H. and Sartor R. B. (1994). Cytokine regulation of experimental intestinal inflammation. Current Opinion in Gastroenterology 10, 625–632.

Klijn N., Weerkamp, A. H., and de Vos W. M. (1995). Genetic marking of Lactoccocus lactis shows its survival in the human gastrointestinal tract. Appl. Environ. Microbiol. 61 (7), 2771–2774.

Kojouharoff G., Hans W., Obermeier F., Männel D. N., Andus T., Schölmerich J., Gross V. and Falk W. (1997). Neutralisation of tumor necrosis factor (TNF) but not of IL-1 reduces inflammation in chronic dextran sulphate sodium-induced colitis in mice. Clin. Exp. Immunol. 107, 353–358.

Lefebvre, O., Wolf, C., Kédinger, M., Chenard M.-P., Tomasetto, C., Chambon, P. and Rio, M.-C. (1993). The mouse one P-domain (pS2) and two P-domain (mSP) genes exhibit distinct patterns of expression. J. Cell. Biol. 122, 191–198.

Liu, D., I. el-Hariry, Karayiannakis A J, Wilding J, Chinery R, Kmiot W, McCrea P D, Gullick W J, Pignatelli M. (1997). "Phosphorylation of beta-catenin and epidermal growth factor receptor by intestinal trefoil factor." Lab Invest 77 (6): 557–63.

MacDermott R. P. (1989). Alterations in serum immunoglobulin G subclasses in patients with ulcerative colitis and Crohn's disease. Gastroenterology 96, 764–768.

Maeda S. and Gasson J. M. (1986). Cloning, expression and location of the *Streptococcus lactis* gene for phospho-B-D-galactosidase. J. Gen. Microbiol. 132, 331–340.

Playford R J, Marchbank T, Goodlad R A, Chinery R A, Poulsom R, Hanby A M (1996). Transgenic mice that overexpress the human trefoil peptide pS2 have an increased resistance to intestinal damage. Proc Natl Acad Sci USA. 93, 2137–2142.

Robinson K., Chamberlain L. M., Schofield K. M., Wells J. M., Le Page R. W. (1997). Oral vaccination of mice against tetanus with recombinant *Lactococcus lactis*. Nature Biotechnol. 15, 653–657.

Sartor R. B. (1995). Inflammatory Bowel Disease: Current concepts of the etiology and pathogenesis of ulcerative colitis and Crohn's disease. Gastroenterology Clinics of North America Vol. 24, 475–507. W.B. Saunders Company, Philadelphia.

Sartor R. B. (1995). Inflammatory Bowel Disease: Microbial factors in the pathogenesis of Crohn's disease, ulcerative colitis and experimental intestinal inflammation. Gatroenterology Clinics of North America. Vol. 24, 96–124. W.B. Saunders Company, Philadelphia.

Steidler L., Wells J. M., Raeymaekers A., Vandekerckhove J., Fiers W. and Remaut E. (1995). Secretion of biologically active murine interleukin-2 by *Lactococcus lactis* subsp. *lactis*. Appl. Environ. Microbiol. 61, 1627–1629.

Studier F. W. and Moffatt B. (1986) Use of bacteriophage T7 RNA polymerase to direct selective high-level expression of cloned genes. J. Mol. Biol. 189, 113–130.

Tan X.-D., Hsueh W., Chang H., Wei, K. R. and Gonzalez-Crussi F. (1997) Characterization of a putative receptor for intestinal trefoil factor in rat small intestine: Identification by in situ binding and ligand blotting. Biochem. Biophys. Res. Comunications 237, 673–677.

Tran C. P., Cook G. A., Yeomans N. D., Thim L. and Giraud A. S. (1999). Trefoil peptide TFF2 (spasmolytic polypeptide) potently accelerates healing and reduces infammation in a rat model of colitis. Gut 44, 636–642.

van Asseldonck M., Rutten G., Oteman M., Siezen R. J., de Vos W. M. and Simons G. (1990). Cloning of usp45, a gene encoding a secreted protein from *Lactococcus lactis* subsp. *lactis* MG1363. Gene 95, 155–160.

Waterfield N. R., Le Page R. W. F., and Wells J. M. (1995). The isolation of lactococcal promoters and their use in investigating bacterial luciferase synthesis in *Lactococcus lactis*. Gene 165, 9–15.

Wells J. M., Wilson P. W. and Le Page R. W. F (1993a). Improved cloning vectors and transformation procedure for *Lactococcus lactis*. J. Appl. Bacteriol. 74, 629–636.

Wells J. M., Wilson P. W., Norton P. M., Gasson M. J. and Le Page R. W. F. (1993b). *Lactococcus lactis*: high-level expression of tetanus toxin fragment C and protection against lethal challenge. Mol. Microbiol. 8, 1155–1162.

Wells J. M., Wilson P. W., Norton P. M., and Le Page R. W. F. (1993c). A model system for investigation of heterologous protein secretion pathways in *Lactococcus lactis*. Appl. Environ. Microbiol. 59, 3954–3959.

Wells J. M. and Schofield K. M. (1996). Cloning and expression vectors for lactococci. NATO ASI Series, Vol. H 98, 37–62. Lactic Acid Bacteria: Current Advances in Metabolism, Genetics and Applications. T. F. Bozoglu & B. Ray (Eds). Springer-Verlag, Berlin, Heidelberg.

Wong, W. M. (1999). Trefoil peptides. Gut 44: 890–895.

Wright N. A., Poulsom R., Stamp G. W., Hall P. A., Jeffery R. E., Longcroft J., Rio M. C., Tomasetto C and Chambon P. (1990). Epidermal growth factor (EGF/URO) induces expression of regulatory peptides in damaged human gastrointestinal tissues. J. Pathol. 162, 279–284.

What is claimed is:

1. A method of treatment of a colon disorder in an individual comprising oral administration of a therapeutically effective amount of a recombinant food grade gram-positive bacterium expressing a trefoil peptide in the colon of said individual.

2. The method of claim 1, wherein the colon disorder involves lesions.

3. The method of claim 1, wherein the recombinant food grade gram-positive bacterium is a lactic acid fermenting bacterium.

4. The method of claim 3, wherein the lactic acid fermenting bacterium is *Lactococcus* or *Lactobacillus*.

5. The method of claim 4, wherein the *Lactococcus* is *Lactococcus lactis*.

6. The method of claim 1, wherein the trefoil peptide is are TFF1 peptide.

7. The method of claim 1, wherein the colon disorder is Crohn's disease (enteritis regionalis), ulcerative colitis (colitis ulcerosa) or acute colitis.

8. The method of claim 1, wherein the oral administration is by a gastric catheter.

9. The method of claim 1, wherein the recombinant food grade gram-positive bacterium comprises a recombinant vector comprising coding sequence of said trefoil peptide under the control of a suitable promoter sequence and a suitable secretion signal sequence.

10. The method of claim 1, wherein the recombinant food grade gram-positive bacterium comprises the nucleotide sequence of SEQ ID NO. 1, SEQ ID NO. 2, or SEQ ID NO. 3.

11. The method of claim 1, wherein the therapeutically effective amount of said recombinant food grade gram-positive bacterium is at least $10^8$ cells of said bacterium.

12. The method of claim 1, wherein the individual is a human or an animal.

* * * * *

UNITED STATES PATENT AND TRADEMARK OFFICE
CERTIFICATE OF CORRECTION

| | |
|---|---|
| PATENT NO. | : 7,220,418 B1 |
| APPLICATION NO. | : 10/030390 |
| DATED | : May 22, 2007 |
| INVENTOR(S) | : Wolfgang Christian Hans, Lothar Steidler and Erik René Remaut |

It is certified that error appears in the above-identified patent and that said Letters Patent is hereby corrected as shown below:

Claim 6, column 33, line 56, delete "are".

Signed and Sealed this

Sixteenth Day of October, 2007

JON W. DUDAS
*Director of the United States Patent and Trademark Office*